(12) United States Patent
During

(10) Patent No.: US 7,935,333 B2
(45) Date of Patent: May 3, 2011

(54) METHOD AND COMPOSITIONS FOR MODIFYING TARGET RECEPTOR FUNCTION ASSOCIATED WITH NEUROLOGICAL DISORDERS

(75) Inventor: Matthew J. During, Philadelphia, PA (US)

(73) Assignee: Auckland Technology Enabling Corporation, Wellington (NZ)

( * ) Notice: Subject to any disclaimer, the term of this patent is extended or adjusted under 35 U.S.C. 154(b) by 0 days.

(21) Appl. No.: 10/776,780

(22) Filed: Feb. 10, 2004

(65) Prior Publication Data
US 2004/0131596 A1    Jul. 8, 2004

Related U.S. Application Data

(62) Division of application No. 09/491,896, filed on Jan. 24, 2000, now abandoned.

(60) Provisional application No. 60/116,748, filed on Jan. 22, 1999, provisional application No. 60/127,142, filed on Mar. 31, 1999.

(51) Int. Cl.
*A01N 63/00* (2006.01)
*A01N 65/00* (2006.01)
*A61K 48/00* (2006.01)
*C12N 15/00* (2006.01)

(52) U.S. Cl. .................. 424/93.2; 424/93.1; 435/320.1; 514/44 R

(58) Field of Classification Search .................. 424/93.1, 424/93.2; 536/23.1; 514/44
See application file for complete search history.

(56) References Cited

U.S. PATENT DOCUMENTS

| | | | |
|---|---|---|---|
| 5,532,265 A | 7/1996 | Gijbels et al. | |
| 5,753,624 A | 5/1998 | McMichael et al. | |
| 5,827,819 A | 10/1998 | Yatvin et al. | |
| 5,851,996 A | 12/1998 | Kline | |

FOREIGN PATENT DOCUMENTS
CA        2087738        7/1994

OTHER PUBLICATIONS

Babiuk, LA. Vaccine 1 7: 1587-1595, 1999.*
Verma et al. (1997) Nature, vol. 389, p. 239.*
Pfeifer and Verma (2001) Annu. Rev. Genomics. Hum. Genet. 2:177-211.*
Johnson-Saliba et al. (2001) Curr. Drug Targets 2:371-99.*
Shoji et al. (2004) Current Pharmaceutical Design 10 :785-796.*
McCluskie et al. (1999) Mol. Med. 5:287-300.*
Lissin et al. (1998) PNAS 95:7097-7102.*
Kammesheidt et al. (1996) Transduction of hippocampal CA1 by adenovirus in vivo. Brain Research 736: 297-304.*
Charles, V et al. "Atropy of Cholinergic Basal Forebrain Neurons Following Excitotoxic Cortical Lesions is Reversed by Inravenous Administration of an NGF Conjugate", Brain Research, vol. 728, pp. 193-203 (1996).
During, M et al. "Peroral Gene Therapy of Lactose Intolerance Using an Adeno-Associated Virus Vector", Nature Medicine, vol. 4, No. 10, pp. 1131-1135 (1998).
Lobell, A. et al. "Vaccination with DNA Encoding an Immunodiminant Myelin Basic Protein Peptide Targeted to Fc of Immunoglobulin G Suppresses Experimental Autoimmune Encephalomyelitis", Journal of Experimental Medicine, vol. 187, No. 9, pp. 1543-1548, (1998).
Shehr, R. "New Treatments for Acute Stroke", Nature Biotechnology, vol. 14, pp. 1549-15454 (1996).
Schenk, D. et al. Immunization with Arnyyloid-β Attenuates Alzheimer-Disease-Like Pathology in the PDAPP Mouse', Nature, vol. 400, pp. 173-177 (1999).
Stanton, P.K. et al. "A Monoclonal Antibody Which Mimicks Glycine Actions on N—Methyl-D-Aspartate Receptors Has Complex Effects on Channel Activation and Neuronal Sensitivity to Hypoxia" Society for Neuroscience Abstracts, vol. 16, No. 1, pp. 88 (1990).
Sun, F. And Faden, A., "Pretreatment With Antisense Oligodeoxynucleotides Directed Against the NMDA-R1 Receptor Enhances Survival and Behavioral Recovery Following Traumatic Brain Injury in Rats" Brain Rsearch, vol. 693, pp. 163-168 (1995).
Wahlestedt, C. et al. "Antisense Oligodeoxynucleotides to NMDA-R1 Receptor Channel Protect Cortical Neurons From Excitotoxicity and Reduce Focal Ischaemic Infarctions", Nature, vol. 363, pp. 260-263 (1993).

* cited by examiner

Primary Examiner — Anne-Marie Falk
(74) Attorney, Agent, or Firm — Thomas J. Engellenner; Nutter McClennen & Fish LLP

(57) ABSTRACT

A method of treating or preventing development of a neurological disorder has been developed wherein a subject with the disorder, or at risk of developing a disorder, is vaccinated against a brain protein or antigen. Alternatively, the antibodies can be directly administered to the individual in need of treatment thereof. Animal studies demonstrate potent efficacy in the treatment of epilepsy, stroke and cognition in animal models vaccinated against the NMDA receptor.

13 Claims, 13 Drawing Sheets

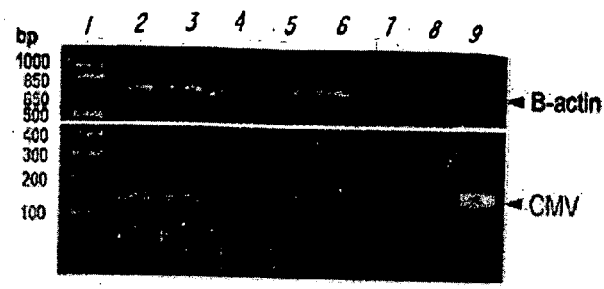
*FIG. 1B*
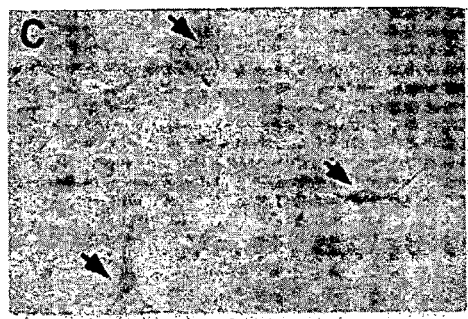 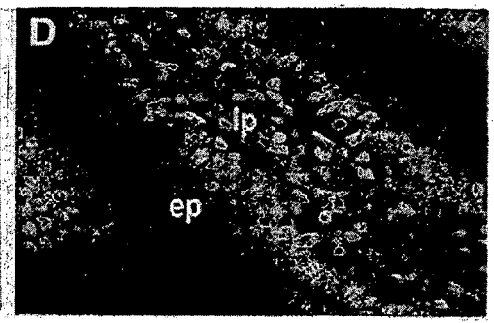
*FIG. 1C*  *FIG. 1D*
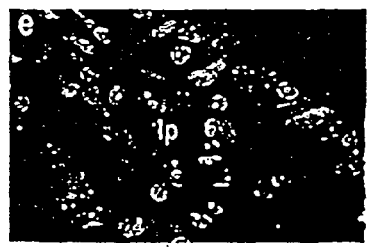 
*FIG. 1E*  *FIG. 1F*
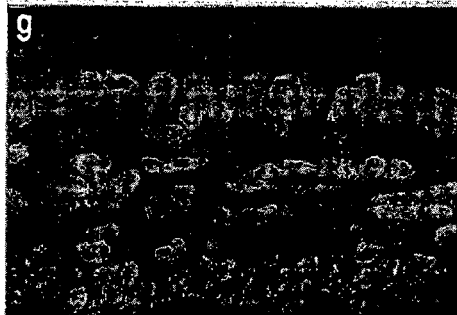 
*FIG. 1G*  *FIG. 1H*

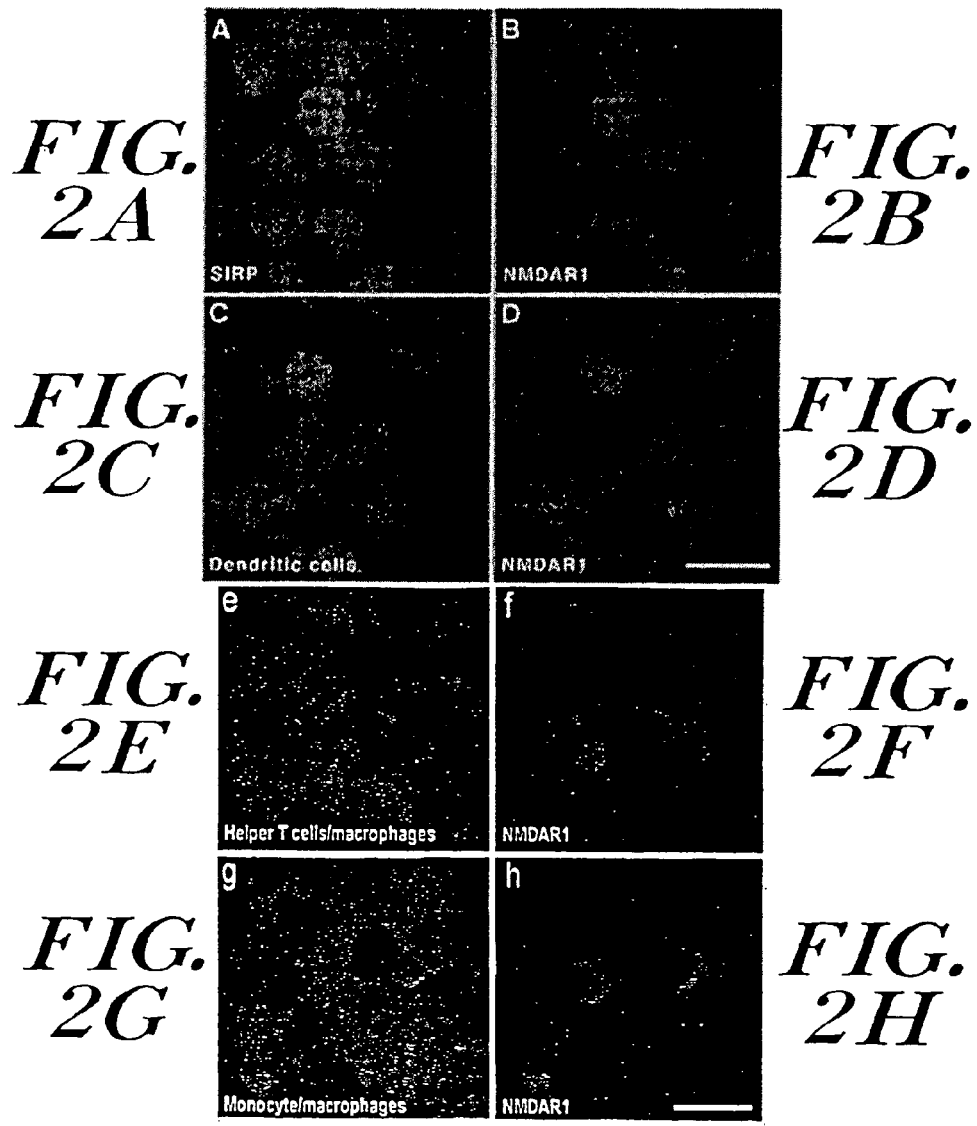

a
AAV lac
AAVNMDAR1 - no SE
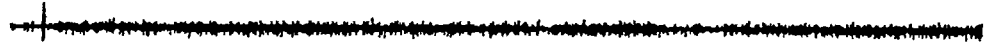
AAVNMDAR1-SE, hippocampal injury
AAVNMDAR1-SE, no hippocampal injury
1 mV
1 min
*FIG. 4*

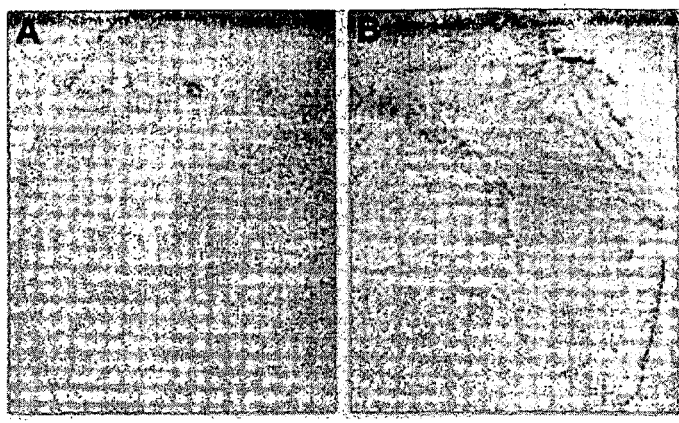
*FIG.6A*  *FIG.6B*
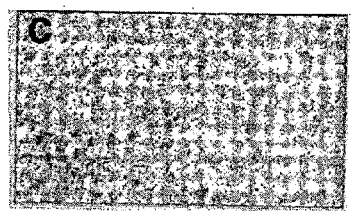 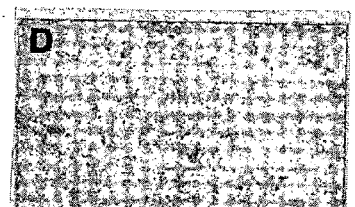
*FIG.6C*  *FIG.6D*
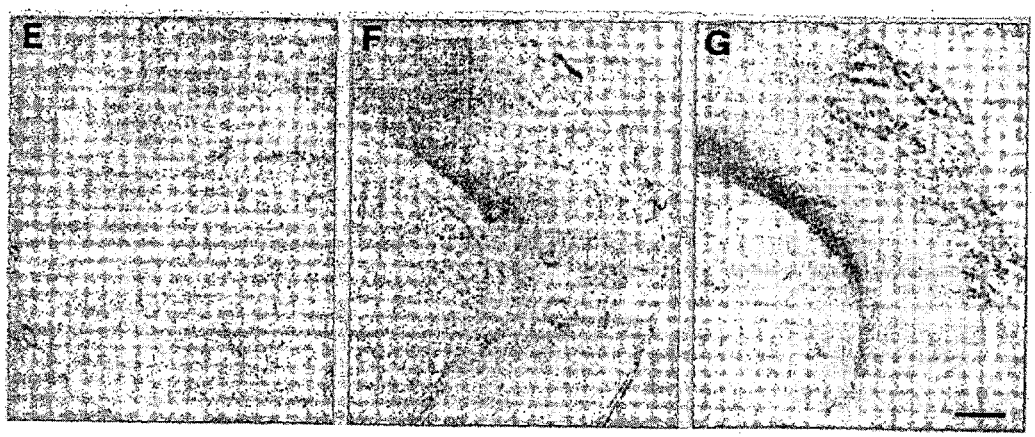
*FIG.6E*  *FIG.6F*  *FIG.6G*

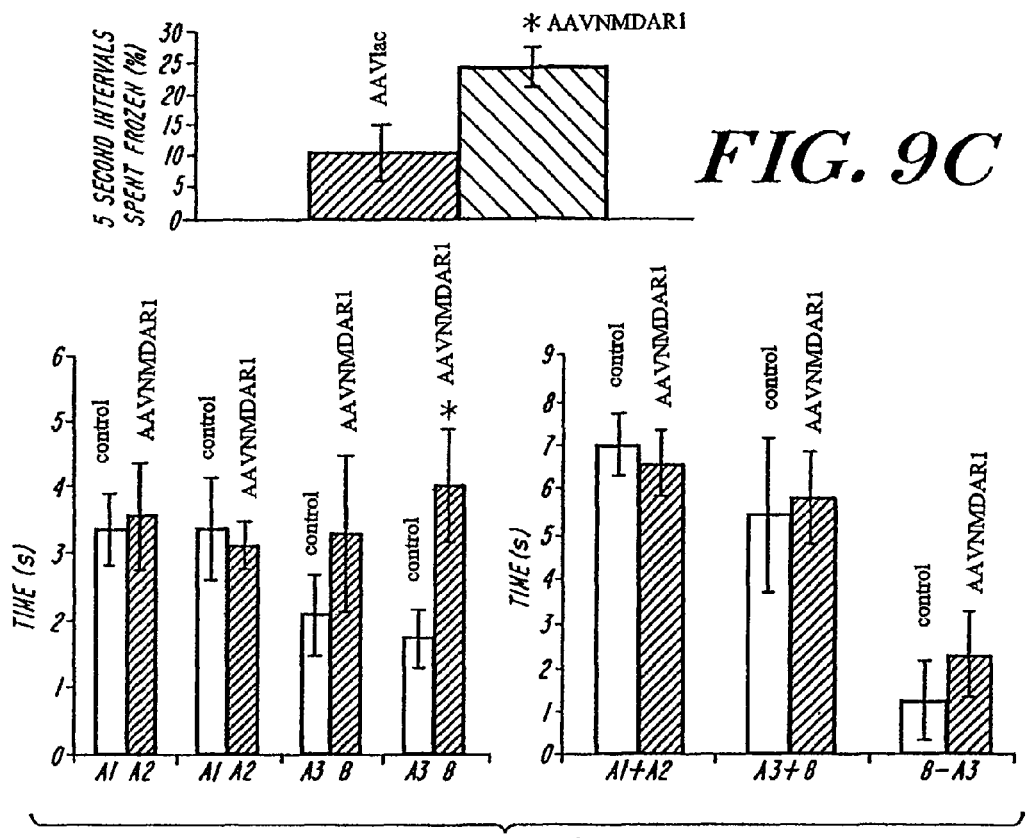
FIG. 9C
FIG. 9D
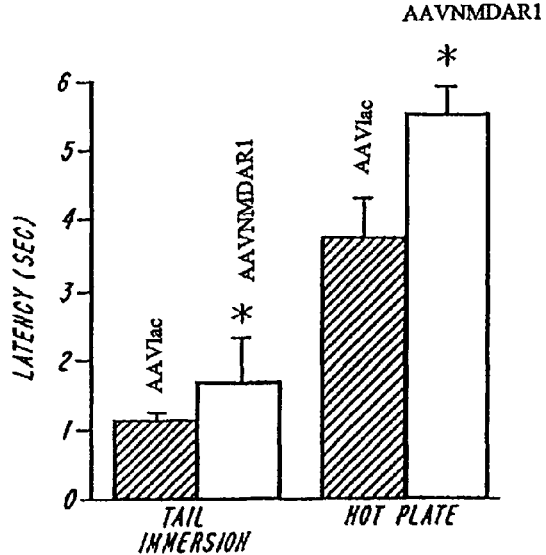
FIG. 10

METHOD AND COMPOSITIONS FOR MODIFYING TARGET RECEPTOR FUNCTION ASSOCIATED WITH NEUROLOGICAL DISORDERS

RELATED CASE INFORMATION

The present invention is a divisional of U.S. patent application Ser. No. 09/491,896, filed Jan. 24, 2000 now abandoned, which claims priority to U.S. Provisional Application No. 60/116,748, filed Jan. 22, 1999 entitled: Vaccine-Mediated Treatment of Neurological Disorders and U.S. Provisional Application No. 60/127,142, filed Mar. 31, 1999 entitled: Vaccine-Mediated Treatment of Neurological Disorders.

BACKGROUND OF THE INVENTION

The present invention is generally in the field of methods and compositions of treatment of neurological disorders, such as epilepsy and stroke, and neuroendocrine disorders, such as obesity. The present invention is also in the field of methods and compositions for modulating gene expression, such as gene expression of the N-methyl-D-aspartate (NMDA) receptor and the transcription factor, Krox-24.

Methods for treating a variety of neurological disorders have focused on the use of pharmaceutical agents which interact with neurological receptors such as the NMDA receptor, neurotransmitter transporters, such as the serotonin or dopamine transporters, various ion channels, or compounds which act to supplement or replace a neurotransmitter such as dopamine. Numerous treatments have been proposed for treatment of disorders such as Alzheimer's, Parkinson's and damage due to stroke, all without lasting success.

Due to NMDA receptors central involvement in the cascade leading to neuronal death following a variety of cerebral insults, pharmacological NMDA receptor antagonists have been evaluated for potential clinical utility. These drugs have shown to be effective in many experimental animal models and some of the compounds have moved into clinical trials (Schehr (1996) *Nat. Biotechnol.* 14:1549-1554). The initial enthusiasm for this approach has, however, waned as the therapeutic ratio for most NMDA antagonists is poor since at clinically effective doses they have been associated with significant adverse effects thereby limiting their utility (Schehr (1996) *Nat. Biotechnol.* 14:1549-1554).

An alternative approach to modify the function of brain proteins has been the use of antisense oligonucleotides or RNA antisense expressing vectors as well as local application of antibodies targeting the specific protein. Some of these approaches have been used to block or translationally suppress NMDA receptor expression and appear effective in a variety of model systems (Wahlestedt et al. (1993) *Nature* 363:260-263; Sun and Faden (19950 *Brain Res.* 693:163-168). However, these therapies generally have transient and limited efficacy.

Therefore a need exists to provide an alternative method of treatment for neurological disorders such as epilepsy, stroke, neuropsychiatric and neurodegenerative disorders. A need also exists to target specific antigens within the brain and modify their function.

SUMMARY OF THE INVENTION

The invention is based on the surprising discovery that one can immunize a subject with, or at risk of developing, epilepsy, stroke or other neurological disorder, against an antigen, e.g., the NMDA receptor, preferably using a genetic vaccine encoding the NMDA receptor as the immunizing agent, to treat or limit the development of the neurological disorder. Antibodies are produced which are immunoreactive to the antigen, for example, the NMDA receptor and can cross the blood brain barrier, although at very low levels other than during injury or due to a disease process or excessive neuronal activity. When the blood-brain-barrier is compromised, the transfer of the antibody into the brain increases significantly. Alternatively, the antibodies can be administered (passive transfer of immunity) to achieve a similar result. Antibodies that can be administered include humanized antibodies, monoclonal antibodies, polyclonal antibodies, or antibody fragments. The invention also features methods and compositions for treating, or preventing the onset of neuroendocrine disorders, such as, obesity by modifying target molecules involved in the regulation of such disorders. The invention also provides methods of modifying target genes or target proteins and processed involving such targets.

Accordingly, in one aspect, the invention features method for treating a neurological disorder in a subject comprising:

administering a vaccine comprising a therapeutically effective amount of an antigen, wherein the antigen elicits the production of antibodies in the circulatory system of the subject, or a composition comprising a therapeutically effective amount of an isolated antibody, or an antibody portion, wherein the antibodies bind to, and modify the function of a target protein in the central nervous system, to thereby ameliorate or prevent the onset of a neurological disorder in the subject.

In one embodiment, the antibodies pass across the blood-brain barrier into the central nervous system facilitated by injury, disease or excessive neuronal activity.

In one embodiment, the disorder is selected from the group consisting of epilepsy, stroke, Alzheimer's, Parkinson's, dementia, Huntington's disease, amyloid lateral sclerosis and depression. In a preferred embodiment, the neurological disorder is stoke. In another preferred embodiment, the neurological disorder is epilepsy.

In one embodiment, the vaccine comprises an antigen selected from the group of neurotransmitters, neuroreceptors, transporters, ion channels, signal transduction molecules, enzymes involved in the synthesis or degradation of neurotransmitters, growth factors, transcription factors, and cell surface molecules. In a preferred embodiment, the antigen is an NMDA receptor. In a more preferred embodiment, the antigen is NMDAR1.

In one embodiment, the vaccine is selected from the group consisting of a viral vector vaccine, a DNA vaccine, a peptide vaccine and a crude antigen vaccine, or a combination thereof. In another embodiment, the vaccine is a viral vector vaccine comprising a viral vector selected from the group consisting of an RNA viral vector and a DNA viral vector. The viral vector vaccine comprises a viral vector selected from the group consisting of an adenovirus vector, a herpes virus vector, a parvovirus vector, and a lentivirus vector. In a preferred embodiment, the viral vector is an adeno-associated virus vector.

In one embodiment, the step of administering a composition comprising a therapeutically effective amount of an isolated antibody, or an antibody portion, further comprises administering an antibody, or an antibody portion elicited in a mammal for administration to the subject. In another embodiment, the isolated antibody, or antibody portion is administered directly to the central nervous system.

In one embodiment, the isolated antibody, or an antibody portion is selected from the group consisting of a monoclonal antibody, a polyclonal antibody, a recombinant antibody, a chimeric antibody, a humanized antibody, an Fab fragment, an F(ab')$_2$ fragment and a single chain Fv fragment.

In another embodiment wherein the isolated antibody, or antibody portion is selected from the group consisting of an anti-NMDA antibody, an anti-GluR antibody, an anti-NK-1 antibody, an anti-dopamine transporter antibody and anti-glutamic acid decarboxylase antibody. In a preferred embodiment, the isolated antibody, or an antibody portion is an anti-NMDA antibody. In a more preferred embodiment, the isolated antibody, or an antibody portion is an anti-NMDAR1 antibody. In another preferred embodiment, the isolated antibody, or antibody portion is an anti-GluR antibody. In a more preferred embodiment, the isolated antibody is an anti-GluR4 antibody or an anti-GluR6 antibody.

In another aspect, the invention features a method for modifying the function of a target protein in the central nervous system of a subject comprising:

administering a vaccine comprising a therapeutically effective amount of an antigen, wherein the antigen elicits the production of antibodies in the circulatory system of the subject, or a composition comprising a therapeutically effective amount of an isolated antibody, or an antibody portion, wherein the antibodies bind to, and modify the function of a target protein in the central nervous system, to thereby modify the function of the target protein.

In one embodiment, the antibodies pass across the blood-brain barrier into the central nervous system facilitated by injury, disease or excessive neuronal activity.

In one embodiment, the target protein is selected from the group of neurotransmitters, neuroreceptors, transporters, ion channels, signal transduction molecules, enzymes involved in the synthesis or degradation of neurotransmitters, growth factors, transcription factors and cell-surface molecules.

In one embodiment, the vaccine comprises an antigen selected from the group of neurotransmitters, neuroreceptors, transporters, ion channels, signal transduction molecules, enzymes involved in the synthesis or degradation of neurotransmitters, growth factors, transcription factors and cell surface molecules. In a preferred embodiment, the antigen is selected from the group consisting of an NMDA receptor, a GluR receptor, an NPY neuropeptide, galanin, an NK-1 receptor, a dopamine transporter and glutamic acid decarboxylase. In a more preferred embodiment, the antigen is an NMDA receptor. In the most preferred embodiment, the antigen is NMDAR1.

In another aspect, the invention features a method for improving cognition in a subject comprising:

administering a vaccine comprising a therapeutically effective amount of an antigen, wherein the antigen elicits the production of antibodies in the circulatory system of the subject, or a composition comprising a therapeutically effective amount of an isolated antibody, or an antibody portion, wherein the antibodies binds to, and modify the function of a target protein in the central nervous system, to thereby improve cognition of a subject.

In one embodiment, the antibody or antibody portion is an anti-NMDA antibody that binds to the NMDA receptor and upregulates NMDA receptor expression. In another embodiment, the antibody binds to the NMDA receptor and decreases Krox-24 expression.

In another aspect, the invention features a method for treating a subject with a neuroendocrine disorder, or at the risk of developing a neuroendocrine disorder comprising:

administering a vaccine comprising a therapeutically effective amount of an antigen to a subject, wherein the antigen elicits the production of antibodies in the circulatory system of the subject, or a composition comprising a therapeutically effective amount of an isolated antibody, or an antibody portion, wherein the antibodies bind to, and modifies the function of a target protein in the central nervous system, to thereby ameliorate the neuroendocrine disorder, or to prevent the onset of the neuroendocrine disorder in the subject.

In one embodiment, the neuroendocrine disorder is obesity. In one embodiment, the antigen is selected from the group consisting of neuropeptide-Y (NPY), galanin, cocaine- and amphetamine-regulated transcript (CART), orexin, thyrotropin-releasing hormone (TRH), leptan, corticotropin-releasing hormone (CRH) and pro-opiomelanocortin (POMC). In a preferred embodiment, the antigen is neuropeptide Y or galanin.

In one embodiment, the antibody is selected from the group consisting of anti-NPY antibody, anti-galanin antibody, anti-CART antibody, anti-orexin antibody, anti-TRH antibody, anti-leptan antibody, anti-CRH antibody, and anti-POMC antibody. In a preferred embodiment, the antibody is an anti-NPY antibody or an anti-galanin antibody. In one embodiment, the target protein is selected from the group consisting of NPY neuropeptide and galanin.

In another aspect, the invention features a pharmaceutical composition comprising a therapeutically effective amount of an antigen capable of eliciting the production of antibodies in the circulatory system of the subject, or a therapeutically effective amount of an isolated antibody, or an antibody portion, wherein the antibodies bind to, and modify the function of a target protein in the central nervous system.

In yet another aspect, the invention features a genetic vaccine comprising an antigen and a pharmaceutical acceptable carrier. In one embodiment, the genetic vaccine comprises an antigen is selected from the group consisting of neurotransmitters, neuroreceptors, transporters, ion channels, signal transduction molecules, enzymes involved in the synthesis or degradation of neurotransmitters, growth factors and transcription factors. In preferred embodiment, the antigen is an NMDA receptor. In a more preferred embodiment, the antigen is NMDAR1.

BRIEF DESCRIPTION OF THE DRAWINGS

FIG. 1B is an agarose gel showing PCR amplification of the CMV promoter from genomic DNA extracted from the intestine of AAVNMDAR1-vaccinated and AAVlac-vaccinated rats;

FIG. 1C is a photograph showing transduction of HEK 293 cells by AAVNMDAR1 virus analyzed by NMDAR1 immunocytochemistry;

FIGS. 1D-1F are photographs of intestinal cells four weeks following peroral AAVNMDAR1 administration using double immunofluorescence analysis with propidium iodide to show the lamina propria (lp) and epithelial (ep) cell layers. NMDAR1 immunohistochemistry showed NMDAR1 protein expression within these two regions;

FIG. 1G is a photograph of intestinal cells showing lack of NMDAR1 protein expression in AAVlac-treated animals at 4 weeks or 5 months (not shown) following peroral AAVNMDAR1 administration;

FIG. 1H is a photograph of intestinal cells 5 months following peroral AAVNMDAR1 administration;

FIGS. 2A-2H are photographs showing NMDAR1 protein expression in lamina propria. Double label immunofluorescent staining combined with acridine orange counterstaining was used to visualize nuclei showed colocalization of NMDAR1 protein (FIG. 2B, FIG. 2D, FIG. 2F, and FIG. 2H) with antibodies to gut cell markers (FIG. 2A) SIRP, (FIG. 2C) dendritic cells, (FIG. 2E) helper T cells/macrophages, and (FIG. 2G) monocyte/macrophages;

FIG. 4 shows electroencephalograph (EEG) recordings displaying the kainate induced seizure damage in the hippocampus and the neuroprotective effect on status epilepticus (SE) in AAVNMDAR1 treated animals;

FIG. 5C is a high powered image of the CA3 region in (FIG. 5B) compared to the same region under basal conditions (arrows, FIG. 5D).

FIGS. 5E-5G are images of the CA3 region, and FIGS. 5H-5J are images of the hilar region, demonstrating only AAVNMDAR1 purified IgG showed a selective immunoreactive staining pattern which was similar to that found with a commercial polyclonal NMDAR1 antibody (FIGS. 5G, and 5J), while both naïve and AAVlac IgG (FIGS. 5F, and 5H) produced only low level background staining FIGS. 6A-6G are photographs of the cortex and stratium demonstrating the reduced ischemic damage in cortex and stratium of AAVNMDAR1-vaccinated rats following middle cerebral artery occlusion;

FIG. 9C demonstrates the data from the contextual fear conditioning test for AAVlac-treated (narrowly spaced upward sloping lines) and AAVNMDAR1-vaccinated animals (widely spaced downward sloping lines) (*p=0.025);

FIG. 9D demonstrates the data from the Spontaneous Object Recognition test in control (solid white) and AAVNMDAR1-vaccinated animals (narrowly spaced upward sloping lines);

FIG. 10 is a bar chart demonstrating the effect of vaccination with AAVNMDAR1 on nociception. The latency for escape responses for the tail immersion test, and the latency for escape responses or hindpaw licking in the hot plate test for AAVlac-treated (black bars), and AAVNMDAR1-vaccinated (white bars) animals. Each bar represents the mean±SEM for all animals in that group (*p=0.04 for tail immersion and p=0.02 for hot plate tests, Student's t-test).

DETAILED DESCRIPTION OF THE INVENTION

Figure 1A:
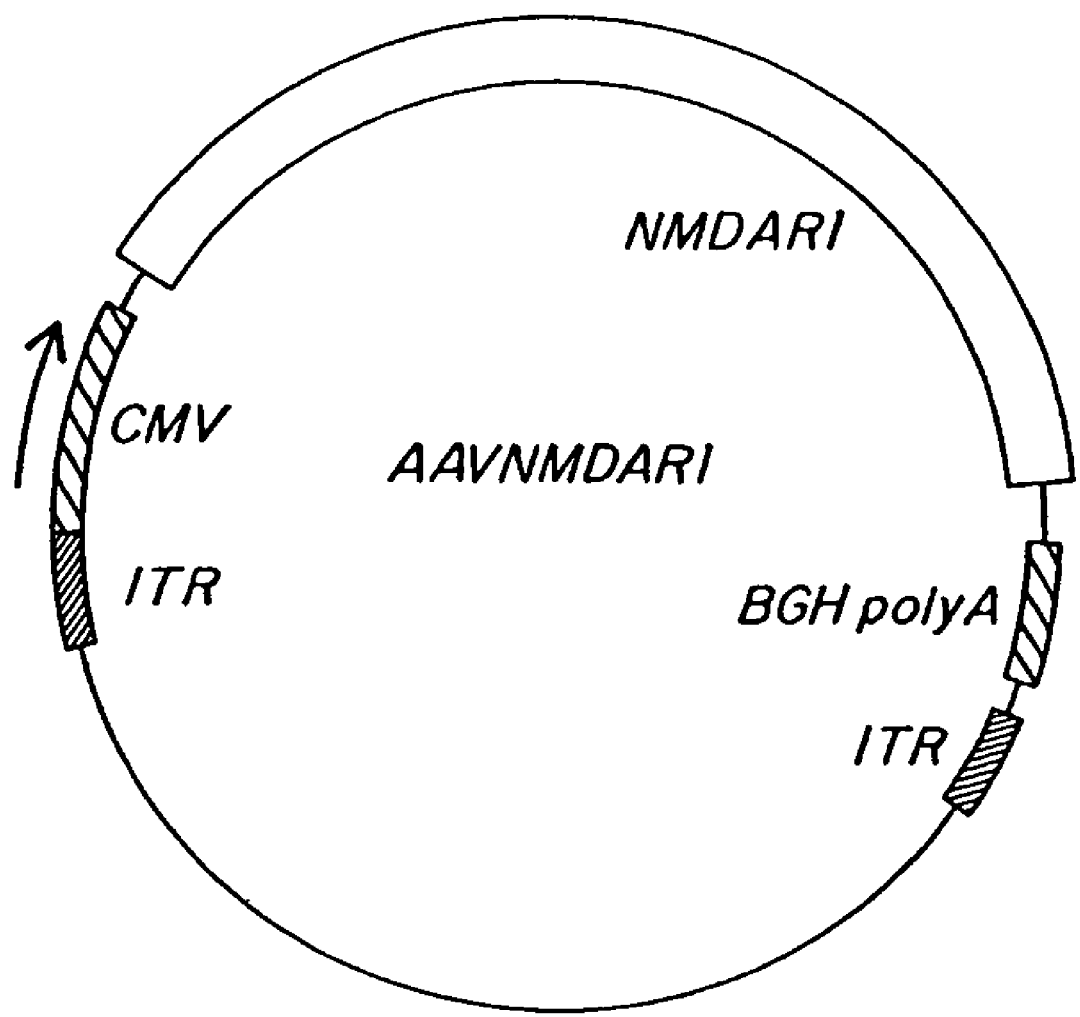
FIG. 1A is a plasmid map of the NMDAR1 construct.
Figure 3A:
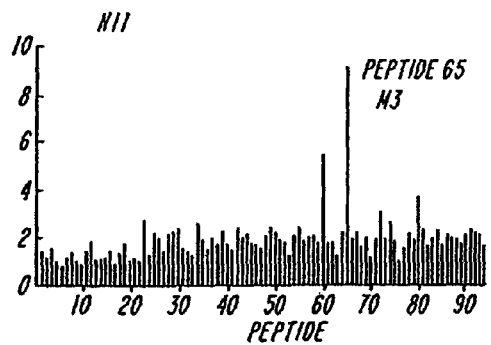
FIGS. 3A-3E are epitope map profiles of five different AAVNMDAR1-treated animals (N11, N19, N21, N52, and N64). Specificity was measured as a ratio between the AAVNMDAR1 signal and mean AAVlac signals for each peptide.
Figure 3B:
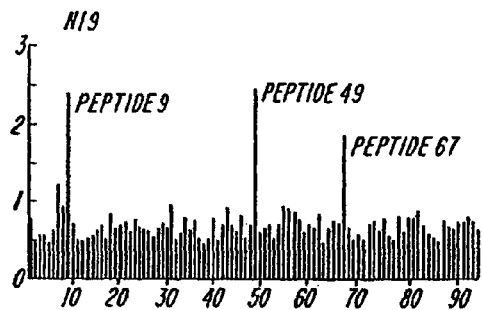
Figure 3C:
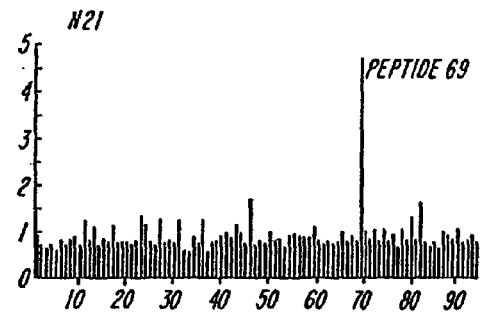
Figure 3D:
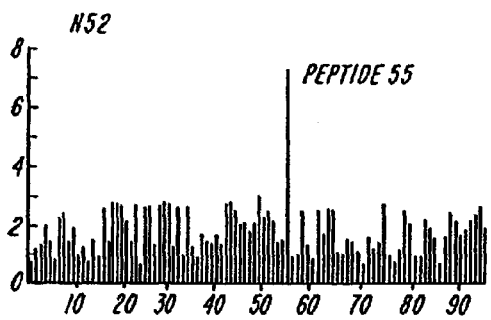
Figure 3E:
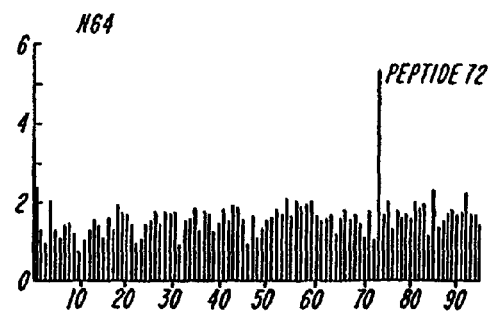

The practice of the present invention employs, unless otherwise indicated, conventional methods of virology, microbiology, molecular biology and recombinant DNA techniques within the skill of the art. Such techniques are explained fully in the literature. (See, e.g., Sambrook, et al. Molecular Cloning: A Laboratory Manual (Current Edition); DNA Cloning: A Practical Approach, Vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); CRC Handbook of Parvoviruses, Vol. I & II (P. Tijessen, ed.); Fundamental Virology, 2nd Edition, Vol. I & II (B. N. Fields and D. M. Knipe, eds.))

So that the invention is more clearly understood, the following terms are defined:

The term "neurological disorder" as used herein refers to an impairment or absence of a normal neurological function or presence of an abnormal neurological function in a subject. For example, neurological disorders can be the result of disease, injury, and/or aging. As used herein, neurological disorder also includes neurodegeneration which causes morphological and/or functional abnormality of a neural cell or a population of neural cells. Non-limiting examples of morphological and functional abnormalities include physical deterioration and/or death of neural cells, abnormal growth patterns of neural cells, abnormalities in the physical connection between neural cells, under- or over production of a substance or substances, e.g., a neurotransmitter, by neural cells, failure of neural cells to produce a substance or substances which it normally produces, production of substances, e.g., neurotransmitters, and/or transmission of electrical impulses in abnormal patterns or at abnormal times. Neurodegeneration can occur in any area of the brain of a subject and is seen with many disorders including, for example, head trauma, stroke, ALS, multiple sclerosis, Huntington's disease, Parkinson's disease, and Alzheimer's disease.

The term "neuroendocrine disorder" as used herein refers to an impairment or absence of a normal neuroendocrine function or presence of an abnormal neuroendocrine function in a subject. For example, neuroendocrine disorders can be characterized by the disturbance in the regulation of mood, behavior, control of feeding behavior and production of substances, such as insulin, neuropeptide-Y (NPY), galanin, cocaine- and amphetamine-regulated transcript (CART), orexin, thyrotropin-releasing hormone (TRH), leptan, corticotropin-releasing hormone (CRH) and pro-opiomelanocortin (POMC).

The term "subject" as used herein refers to any living organism in which an immune response is elicited. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

The term "mammal" as used herein refers to a living organism capable of eliciting a humoral immune response to an antigen. The term subject includes, but is not limited to, nonhuman primates such as chimpanzees and other apes and monkey species, sheep, pigs, goats, horses, dogs, cats, mice, rats and guinea pigs, and the like. The mammal can be used to generate antibodies or antibody portions, that can subsequently be used to vaccinate a subject.

The term "antibody" includes an immunoglobulin molecule comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The term "antigen-binding portion" of an antibody or an "antibody portion" includes fragments of an antibody that retain the ability to specifically bind to an antigen (e.g., NMDA receptor). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); See e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (See e.g., Holliger et al. (1993) *Proc. Natl. Acad. Sci. USA* 90:6444-6448; Poljak, et al. (1994) *Structure* 2:1121-1123).

Still further, an antibody or antigen-binding portion thereof may be part of a larger immunoadhesion molecules, formed by covalent or non-covalent association of the antibody or antibody portion with one or more other proteins or peptides. Examples of such immunoadhesion molecules include use of the streptavidin core region to make a tetrameric scFv molecule (Kipriyanov, et al. (1995) *Human Antibodies and Hybridomas* 6:93-101) and use of a cysteine residue, a marker peptide and a C-terminal polyhistidine tag to make bivalent and biotinylated scFv molecules (Kipriyanov et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein. Preferred antigen binding portions are complete domains or pairs of complete domains.

An "isolated antibody" includes an antibody that is substantially free of other antibodies having different antigenic specificities (e.g., an isolated antibody that specifically binds NMDA is substantially free of antibodies that specifically bind antigens other than NMDA). An isolated antibody that specifically binds NMDA may bind NMDA molecules from other species. Moreover, an isolated antibody may be substantially free of other cellular material and/or chemicals.

The term "autoantibody" as used herein refers an antibody against self-antigen, i.e. an antibody that reacts with an antigen that is the normal component of the body. For example, an antibody produced by the subject against an antigen within the subject. An autoantibody can be elicited as part of the immune response to an antigen. For example, by vaccination of an antigen or a portion of an antigen, that is capable of eliciting an immune response resulting in the production of antibodies against the antigen.

The term "antigen" or "immunogen" is used interchangeably and refers to a substance or a material that is specifically recognized by an antibody and to which an antibody can be generated. The antigen can be a whole molecule or a portion of a molecule that can elicit an immune response. The term antigen is also intended to include a nucleic acid molecule encoding an antigen, or a peptide or polypeptide comprising an antigenic epitope. An antigen or a portion thereof that can elicit an immune response can be determined using standard methods such as epitope mapping. Examples of antigens include, but are not limited to, receptors, transporters, ion channels, neurotransmitters, and the like.

The term "systemic circulatory system" or "systemic circulation" as used herein refers to the art known use of the term. The systemic circulatory system serves to transport blood through the body. The systemic circulatory system can be used to elicit an immune response using an antigen that results in the production of antibodies against the antigen. These antibodies continue to exist and circulate throughout the body.

The term "central nervous system" or "CNS" as used herein refers to the art recognized use of the term. The CNS pertains to the brain, cranial nerves and spinal cord. The CNS also comprises the cerebrospinal fluid, which fills the ventricles of the brain and the central canal of the spinal cord.

The term "modifies" or "modified" are used interchangeably herein and refer to the up-regulation or down-regulation of a target gene or a target protein. The term modifies or modified also refers to the increase, decrease, elevation, or depression of processes or signal transduction cascades involving a target gene or a target protein. A target protein, can be a receptor, for example, an NMDA receptor. Modification to the NMDA receptor may occur when an antibody to the NMDA receptor binds to the NMDA receptor. These modification may directly affect the NMDA receptor, for example modifications that result in an increase in NMDA receptor number. Alternatively, the modifications may occur as an indirect effect of binding to the target protein. For example, binding of the anti-NMDA receptor antibody to the NMDA receptor can also lead to a change in downstream processes involving the NMDA receptor, such as a reduction the expression of the Krox-24 protein. The modifications can therefore be direct modifications of the target protein, or an indirect modification of a process or cascade involving the target protein. Non-limiting examples of modifications includes modifications of morphological and functional processes, under- or overproduction or expression of a substance or substances, e.g., a neurotransmitter, by neural cells, failure of neural cells to produce a substance or substances which it normally produces, production of substances, e.g., neurotransmitters, and/or transmission of electrical impulses.

The term "genetic vaccine" as used herein refers to a vaccine composition comprising one or more antigen(s), or antigen portions that are capable of eliciting an immune response that results in the production of antibodies in the circulatory system of a subject. In particular, the genetic vaccine comprises an antigen or portion thereof, that produces an antibody, which can bind to, and modify the function of a target gene or a target protein, directly or indirectly. The term genetic vaccine is also intended to include a vaccine composition that comprises one or more substances (e.g., neuropeptides, neurotransmitters, and the like) that can bind to, and modulate the function of a target gene or a target protein directly, or indirectly.

The invention is described in more detail in the following subsections:

I. Genetic Vaccines

The brain is generally considered immunoprivileged, although increasing examples of immunological responses to brain antigens, neuronal expression of Major Histocompatibility Class I genes and neurological autoimmunity have been recognized. As demonstrated by the examples, an adeno-associated virus (AAV) vaccine can generate autoantibodies which target a specific brain protein, the NR1 subunit of the N-methyl-D-aspartate receptor. In one embodiment, the genetic vaccine of the invention comprises one or more antigen(s). The antigen is capable of eliciting a humoral response that results in the production of antibodies against the antigen. The antigen, such as NMDAR1, is selected based on the disorder to be treated or prevented. For example, for disorders in which the NMDA receptor plays a major role, such as epilepsy, stroke, brain trauma, depression, dementia, chronic pain, migraine and neurodegenerative disorders including ALS, Huntington's, Parkinson's and Alzheimer's Diseases, the NMDA receptor or a portion thereof is used as the basis for the vaccine. In addition, for Parkinson's Disease, the dopamine transporter is used as the antigen. Other disorders which can be treated include Alzheimer's disease, depression and obesity, using antigens such as the amyloid protein, neurokinin 1 receptor or neuropeptide Y. Other preferred antigens include a GluR receptor (e.g., GluR4, GluR6), an NPY neuropeptide, galanin, an NK-1 receptor, a dopamine transporter and glutamic acid decarboxylase, adenosine kinase, and neurokinin-1 (NK-1). Examples of molecules that can be used as antigens include, but are not limited to, receptors, transporters, ion channels, neurotransmitters, and the like.

(a) Receptors

The location of neurotransmitter receptors at synapses makes them a likely target for alterations during aging and in diseases that alter behavior and cognition. Examples of suitable receptors include, but are not limited to, N-methyl-D-aspartate (NMDA) receptor, neuronal glutamate receptors (GluR's), γ-aminobutyric acid receptors (GABAR's), nicotinic acetylcholine receptors, serotonin receptors, dopamine receptors, and the like. A preferred receptor is the NMDA receptor.

The NMDA is a class of glutamate receptor which is important in the pathology of many neurological disorders. Activation of NMDA receptors increases sodium and calcium conductance, which depolarizes the neuron, thereby increasing the likelihood that the neuron will fire an action potential. NMDA receptors are widely distributed throughout the brain, with a particularly high density in the cerebral cortex and hippocampal formation.

In the central nervous system, NMDA receptors are mediators of glutamatergic excitatory neurotransmission and are of major interest as they are involved in brain development including neuronal migration (Komuro et al. (1993) *Science* 260:95-97) patterning of afferent termination (Bear et al. (1990) *J. Neurosci.* 10:909-925) and several forms of long-term synaptic plasticity (Bliss and Collingridge (1993) *Nature* 361:31-39). Properties of the receptor include calcium permeability, voltage-dependent $Mg^{2+}$ block, and slow channel kinetics (McBain et al. (1994) *Physiol. Rev.* 74:723-760). Molecular cloning has revealed three receptor subunit families, NR1, NR3A and four types of NR2 subunits which in native NMDA receptor channels form hetero-oligomeric complexes (Hollmann and Heinemann (1994) *Ann. Rev. Neurosci.* 17:31-108; Das et al. (1998) *Nature* 393:377-381). NR1 subunits are essential for the formation of functional NMDA receptors, whereas addition of other subunits modify receptor properties (Das et al. (1998) *Supra*; Sheng et al. (1994) *Nature* 368:144-147). In addition to the role of NMDA receptors in brain plasticity and development, they have also been implicated as a mediator of neuronal injury associated with many neurological disorders including stroke, epilepsy, brain trauma, AIDS dementia as well as neurodegenerative disorders (Beal (1992) *Current Opinion in Neurobiology* 2:657-662).

In another embodiment, the receptor is a glutamate receptor (GluR). Neuronal glutamate receptors (GluR's) comprise the predominant excitatory neurotransmitter system in the mammalian central nervous system (Choi (1992) *J. Neurobiol.* 23: 1261). Excessive glutamate receptor stimulation has been linked to subsequent neuronal death. This excitotoxicity is thought to play a role in nervous system destruction after stroke, trauma, epilepsy, Alzheimer's disease, and Huntington's disease. There are numerous subunits that compose the glutamate receptor family. Several subunits of the glutamate receptor have been molecularly cloned (See e.g., Hollmann et al. (1993) *Ann. Rev. Neurosci.* 17: 31-108). These subunits are broadly grouped on the basis of sequence identity. These divisions include cDNAs that encode receptors with NMDA pharmacology and at least nine cDNAs that encode non-NMDA receptor types. This latter group can be subdivided into three groups based upon similarity of primary sequence and/or function. GluR1, GluR2, GluR3, and GluR4 type receptors that are responsive to kainic acid and α-amino-3-hydroxy-5-methyl-4-isoxazole propionate (AMPA) and bind AMPA with high affinity. GluR5, GluR6, and GluR7 type receptors that are responsive to kainic acid only, or bind kainic acid with high affinity.

(b) Neurotransmitters

Neurotransmitters are chemicals in the brain that are used to send messages from one brain cell to another. Neurotransmitters bind to special receptor proteins in the membranes of nerve cells, like a lock in a key, triggering a chemical reaction within the cell. Examples of neurotransmitters include, but are not limited to, dopamine, acetylecholine, and norepharine.

In one embodiment, the neurotransmitter is dopamine. Dopamine is an example of a central nervous system (CNS) neurotransmitter, and is a catecholamine belonging to a class of biogenic amine neurotransmitters, along with norepinephrine, serotonin, and histamine. The catecholamines (particularly dopamine and serotonin) are involved in the control of movement, mood, attention, and endocrine, cardiovascular, and stress responses. Imbalances in neurotransmitter production have been implicated in a variety of mental and physical disorders, such as Parkinson's disease, schizophrenia and psychosis.

Two major families of dopamine receptors have been identified and named the D1 and D2 families. In the D2 family, three distinct receptor subtypes have been identified as D2, D3, and D4. The distribution and concentration of the subtypes of receptors varies in different regions of the brain. D2 subtype receptors are located in both the limbic region of the brain, which is associated with cognition and emotional function, and in the stratium, which is associated with motor effects. D4 receptors are found in higher concentrations in the frontal cortex and limbic regions, which are associated with cognitive and emotional function.

In another embodiment, the neurotransmitter is acetylcholine (ACh) which activates two pharmacologically different receptor types: the nicotinic acetylcholine receptors (nAChR) from the ligand-gated ion channel superfamily, and the muscarinic acetylcholine receptors (mAChR) from the G-protein coupled receptor superfamily (Taylor et al. New York: Pergamon Press, (1990) 166-186; and 122-149). A number of pathologies and/or disease conditions are associated with nAChRs, for example, myasthenia gravis, schizophrenia, Alzheimer's disease, Tourette's disease and nicotine addiction.

In another embodiment, the neurotransmitter is serotonin. Serotonin is a hormone-neurotransmitter and has a role in physiologic processes such as sleep and in pathophysiologic conditions including depression, chronic pain, and migraine, and drug addiction. Serotonin is also a biosynthetic precursor of melatonin. Melatonin is important in temperature regulation, mood, and the sleep-wake cycles. Receptor binding sites for melatonin have been reported in discrete regions of the mammalian brain. Two mammalian melatonin receptors have been identified by expression cloning and shown to have expression patterns consistent with their predicted locations from hormone binding studies.

(c) Transporters

Certain amino acids, such as glutamate and glycine, as well as amino acid derivatives such as γ-aminobutyric acid (GABA), epinephrine and norepinephrine, and histamine, are also used as signaling molecules in higher organisms. For these reasons, specialized transmembrane transporter proteins have evolved in all organisms to recover or scavenge extracellular amino acids (for review see Christensen, (1990), *Physiol. Rev.* 70: 43-77).

These transporter proteins are important for the uptake of extracellular amino acids in the brain and peripheral motor and sensory tissues (see Nicholls & Attwell, (1990), *TiPS* 11: 462-468). Amino acids that function as neurotransmitters must be scavenged from the synaptic cleft between neurons to enable continuous repetitive synaptic transmission. High extracellular concentrations of certain amino acids (including glutamate and cysteine) can cause neuronal cell death, and are associated with a number of pathological conditions, including ischemia, anoxia and hypoglycemia, as well as chronic illnesses such as Huntington's disease, Parkinson's disease, Alzheimer's disease, epilepsy and amyotrophic lateral sclerosis (ALS: see Pines et al. (1992) *Nature* 360: 464-467).

Glutamate is an excitatory neurotransmitter (i.e., excitatory neurons use glutamate as a neurotransmitter). When present in excess (>about 300 mM; Bouvier et al. (1992), *Nature* 360: 471-474; Choi et al., (1987), *J. Neurosci.* 7: 357-358), extracellular glutamate causes neuronal cell death. Glutamate transporters play a pivotal role in maintaining non-toxic extracellular concentrations of glutamate in the brain. Glutamate transporters, for example, excitatory amino acid transporters (EAAT), can also be used in the present invention as antigens. Examples of suitable EAAT neurotransmitters, include but are not limited to EAAT1, EAAT2, EAAT3, EAAT4 and EAAT5 (See e.g., U.S. Pat. No. 5,919, 628 issued to Amara et al.)

(d) Transcription Factors

Polypeptides which can function as transcription factors to activate transcription in prokaryotic cells are well known in the art. Transcription factors comprise at least one DNA binding domain and at least one transcriptional activation domain (e.g., parts of promoters or enhancer sequences). DNA binding domains that bind to specific regulatory sequences are also well known in the art (see, e.g., Keegan et al. (1988), *Science,* 231, 699-704; Hope et al. (1986) *Cell,* 46, 885-894 and Ma et al. (1987) *Cell* 51, 113-119). Transcriptional activation domains found within various proteins have been grouped into categories based upon similar structural features. Types of transcriptional activation domains include acidic transcription activation domains, proline-rich transcription activation domains, serine/threonine-rich transcription activation domains and glutamine-rich transcription activation domains. Antigens of transcription factors may also be used in the invention.

In a preferred embodiment, the transcription factors are those implicated in neuronal activation. Transcription factors implicated in neurological disorders leading to cell death in neurons include c-fos, c-jun, and c-jun N-terminal kinase (JNK) in the in dopamine neurons of the substantia nigra (SN). The increased expression of c-jun is described to be functionally significant in the neuronal cell death, because it is associated with increased c-jun N-terminal kinase (JNK) and phosphorylated c-jun expression (Oo et al. (1999) *J. Neurochem.* 72:557-64 and Chihab et al. (1998) *Brain Res Mol Brain Res* 63:105-120). Other examples of transcription factors important in neurological disorders include protein kinase C (PKC) activity. For example, increased presynaptic protein kinase C activity is associated with by increased glutamate release (Di Luca et al. (1997) *Eur. J. Neurosci.* 9:472-479).

(e) Growth Factors

In another embodiment, the antigen can be a growth factor which can stimulate or retard cell growth. Studies have shown in animal models of neurodegenerative diseases, that delivering a neurotrophic factors, such as nerve growth factor (NGF), which sustains the growth and development of neurons, prevents damage-induced death, and attracts the growth of developing or regenerating axons, to the area of neurodegeneration. Suitable examples of growth factors include, but are not limited to, glial cell line-derived neurotrophic factor (GDNF), ciliary derived neuronotrophic factor (CNTF), brain derived neuronotrophic factor (BDNF), neuronotrophin-3 (NT3), epidermal growth factor (EGF), fibroblast growth factor (FGF), transforming growth factor-α (TGF-α), transforming growth factor-β (TGF-β), platelet derived growth factor (PDGF), (f) Ion channel Proteins Ion channel proteins are mediators of information transfer in the brain, endocrine system, enteric nervous system and neuromuscular junction, modulate ion fluxes that produce voltage changes across cell membranes and simultaneously act as sensors of physiological signals, for example, changes in ligand concentrations and in transmembrane voltage. Ligand-gated ion channels provide a rapid dialogue between cells of the central nervous system, converting a chemical neurotransmitter signal released from one cell into an electrical signal that propagates along the cell membrane of a target cell. Ligand-gated ion channels are multimeric protein complexes with component subunits encoded by related genes.

Numerous families of ligand-gated receptors have been identified and characterized on the basis of sequence identity. Those which form cationic channels include, for example, excitatory nicotinic acetylcholine receptors (nAChRs), excitatory glutamate-activated receptors, the $5\text{-HT}_3$ serotonin receptor, the ATP receptor and the sarcoplasmic ryanodine receptor. Those which form anionic channels include, for example, the inhibitory GABA and glycine-activated receptors.

(g) Signal Transduction Molecules

Reversible phosphorylation of proteins is a prevalent biological mechanism for modulation of enzymatic activity in living organisms. (Tonks et al. (1988), *J. Biol. Chem.* 263: 6722-6730). Such reversible phosphorylation requires both a protein kinase (PK), to phosphorylate a protein at a particular amino acid residue, and a protein phosphatase (PP), to remove the phosphate moieties. See e.g., Hunter, (1995) *Cell*, 80:225-236. One major class of protein kinases are the serine/threonine kinases and a major type of protein phosphatases are protein serine/threonine phosphatases. These protein kinases and phosphatases have been shown to play critical roles in the regulation of metabolism. (See e.g., Cohen, (1992) *Trends Biochem. Sci.*, 17:408-413; Shenolikar, (1994) *Ann. Rev. Cell Biol.*, 10:55-86; Bollen et al. (1992), *Crit. Rev. Biochem. Mol. Biol.* 27:227-281). These enzymes phosphorylate and dephoshphorylate serine and threonine residues of substrate proteins. Preferably, the serine/threonine kinases or serine/threonine phosphatases are those that are involved in neuronal activation.

Another group of protein kinases and phosphatases includes the tyrosine kinases an tyrosine phosphatases. The protein tyrosine kinases and the protein tyrosine phosphatases comprise enzymes that have been implicated in the control of normal and neoplastic cell growth and proliferation. See Fisher et al. (1991), *Science*, 253:401-406. Protein tyrosine kinase (PTK) genes share a high degree of interspecies conservation. (See e.g., Hunter and Cooper, (1985) *Ann. Rev. Biochem.* 54:897-930. PTK enzymes exhibit high specificity for tyrosine, and ordinarily do not phosphorylate serine, threonine, or hydroxyproline. Their roles in cellular processes include, cell-cell contact and cell adhesion, and growth factor and antigen signaling events. Preferably, the tyrosine kinases or tyrosine phosphatases are those that are involved in neuronal activation.

II. Antibodies

Antibodies to the antigens for direct transfer of immunity can also be administered. Antibodies can be generated using standard techniques known in the art and include recombinant antibodies, chimeric antibodies, humanized antibodies, and the like. The antibody may be of animal, e.g., a mouse or rat. Preferably, the antibody is a human antibody. The antibody may be a chimeric antibody (See e.g., Morrison et al., (1984) *Proc Nat. Acad. Sci. U.S.A.* 81: 6851-6855) or a humanized antibody (See e.g., Jones et al. (1986) *Nature* 321: 522-525. Methods of producing antibodies suitable for use in the present invention are well known to those skilled in the art and can be found described in such publications as Harlow & Lane, Antibodies: A Laboratory Manual, Cold Spring Harbor Laboratory (1988), and Asai, Methods in Cell Biology Vol. 37. Antibodies in Cell Biology, Academic Press, Inc. N.Y. (1993).

When antibodies are generated by immunizing animals with an antigen to yield antibody which is not of human origin, the antibodies could elicit an adverse effect if administered to humans. Methods for "humanizing" antibodies, or generating less immunogenic fragments of non-human antibodies, are well known. A humanized antibody is one in which only the antigen-recognized sites, or complementarity—determining hypervariable regions (CDRs) are of non-human origin, whereas all framework regions (FR) of variable domains are products of human genes. These "humanized" antibodies present a lesser xenografic rejection stimulus when introduced to a human recipient.

To accomplish humanization of a selected mouse monoclonal antibody, the CDR grafting method described by Daugherty et al. (1991) *Nucl. Acids Res.* 19:2471-2476, may be used. Briefly, the variable region DNA of a selected animal recombinant anti-idiotypic ScFv is sequenced by the method of Clackson, et al. (1991), *Nature,* 352:624-688. Using this sequence, animal CDRs are distinguished from animal framework regions (FR) based on locations of the CDRs in known sequences of animal variable genes (See e.g., Kabat, et al. (1991) *Sequences of Proteins of Immunological Interest, Fifth Edition*, U.S. Department of Health and Human Services, NIH Publication No. 91-3242). Once the animal CDRs and FR are identified, the CDRs are grafted onto human heavy chain variable region framework by the use of synthetic oligonucleotides and polymerase chain reaction (PCR) recombination. Codons for the animal heavy chain CDRs, as well as the available human heavy chain variable region framework, are built in four (each 100 bases long) oligonucleotides. Using PCR, a grafted DNA sequence of 400 bases is formed that encodes for the recombinant animal CDR/human heavy chain FR protection.

For recombinant production of antibodies, the sequences of human heavy chain constant region genes are known in the art (See e.g., Kabat, et al. *Supra*) and DNA fragments encompassing these regions can be obtained by standard PCR amplification. The heavy chain constant region can be an IgG1, IgG2, IgG3, IgG4, IgA, IgE, IgM or IgD constant region and any allotypic variant therein as described in Kabat et al., supra The sequences of human light chain constant region genes are known in the art and DNA fragments encompassing these regions can be obtained by standard PCR amplification. The light chain constant region can be a kappa or lambda constant region.

To create a scFv gene, the VH- and VL-encoding DNA fragments are operatively linked to another fragment encoding a flexible linker, e.g., encoding the amino acid sequence $(\text{Gly}_4\text{-Ser})_3$, such that the VH and VL sequences can be expressed as a contiguous single-chain protein, with the VL and VH regions joined by the flexible linker (See e.g., Bird et al. (1988) *Science* 242:423-426; Huston et al. (1988) *Proc. Natl. Acad. Sci. USA* 85:5879-5883; McCafferty et al. (1990)

Nature 348:552-554). To express the antibodies, or antibody portions, DNAs encoding partial or full-length light and heavy chains are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). Additionally or alternatively, the recombinant expression vector can encode a signal peptide that facilitates secretion of the antibody chain from a host cell.

The recombinant expression vectors used for antibody production carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; (1990) *Gene Expression Technology: Methods in Enzymology* 185, Academic Press, San Diego, Calif. Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma.

For expression of the light and heavy chains, the expression vector(s) encoding the heavy and light chains can be transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in Kaufman et al. (1982) *Mol. Biol.* 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce portions of intact antibodies, such as Fab fragments or scFv molecules. In addition, bifunctional antibodies may be produced in which one heavy and one light chain are an antibody of the invention and the other heavy and light chain are specific for an antigen other than NMDA by crosslinking an antibody of the invention to a second antibody by standard chemical crosslinking methods.

III. Pharmaceutical Compositions and Pharmaceutical Administration

The antigen, antibodies or antigen-binding portions of the invention can be incorporated into pharmaceutical compositions suitable for administration to a subject. Typically, the pharmaceutical composition comprises an antigen, antibody or antibody portion of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

The antigens, antibodies and antibody-portions of the invention can be incorporated into a pharmaceutical composition suitable for parenteral administration. Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trenhalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans. The preferred mode of administration is parenteral (e.g., intravenous, subcutaneous, intraperitoneal, intramuscular). In a preferred embodiment, the antigen, antibody or antibody-portion is administered by intravenous infusion or injection. In another preferred embodiment, the antibody is administered by intramuscular or subcutaneous injection. In the most preferred embodiment, the antigen, antibody or antibody portion is administered perorally.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antigen, antibody or antibody portion) in the required amount in an appropriate solvent with one or a combination of ingredients enumerated above, as required, followed by filtered sterilization.

Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antigen, antibody or antibody portion of the present invention can be administered by a variety of methods known in the art. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antigen, antibody or antibody portion of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, an antigen, antibody or antibody portion of the invention is coformulated with and/or coadministered with one or more additional therapeutic agents that are useful for treating disorders in which NMDA receptor activity is detrimental. For example, an anti-NMDA antibody or antibody portion of the invention may be coformulated and/or coadministered with one or more additional antibodies that bind other targets (e.g., antibodies that bind other cytokines or that bind cell surface molecules). Furthermore, one or more antigens or antibodies of the invention may be used in combination with two or more of the foregoing therapeutic agents. Such combination therapies may advantageously utilize lower dosages of the administered therapeutic agents, thus avoiding possible toxicities or complications associated with the various monotherapies.

Antigens, antibodies or antibody-portion can be used alone or in combination to treat diseases. For example, the antigen, antibodies, or antibody portion can be used alone or in combination with an additional agent, e.g., an agent which imparts a beneficial attribute to the therapeutic composition e.g., an agent which effects the viscosity of the composition. The combination can also include more than one additional agent, e.g., two or three additional agents if the combination is such that the formed composition can perform its intended function.

The invention is also intended to include one or more combinations of antigens, such that one or more antibodies are produced against the antigens in the systemic circulation of the subject. For example, the first antigen can a portion of the NMDAR1 receptor, and the second antigen can be a portion of the Glu R receptor. Accordingly, antibodies to both NMDAR1 and Glu R receptor can be produced. The skilled artisan will appreciate that any combination of one or more antigen can be used to produce the genetic vaccine of the invention.

The pharmaceutical compositions of the invention may include a "therapeutically effective amount" or a "prophylactically effective amount" of an antigen, antibody or antibody portion of the invention. A "therapeutically effective amount" refers to an amount effective, at dosages and for periods of time necessary, to achieve the desired therapeutic result. A therapeutically effective amount of the antigen, antibody or antibody portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an antigen, antibody or antibody portion of the invention is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

IV Delivery Systems

The invention features a method of using adeno-associated viral vectors (AAV) comprising the NMDA antigen in a genetic vaccine. AAV vectors can be constructed using known techniques to provide at least the operatively linked components of control elements including a transcriptional initiation region, a exogenous nucleic acid molecule encoding an antigen, and a transcriptional termination region. The control elements are selected to be functional in the targeted cell. The resulting construct which contains the operatively linked components can be flanked at the 5' and 3' region with functional AAV ITR sequences.

The preferred AAV is AAV-2 as described by Kotin et al. (1994) *Human Gene Therapy* 5:793-801; Berns "Parvoviridae and their Replication" in Fundamental Virology, 2nd Edition, (B. N. Fields and D. M. Knipe, eds.), although other AAV serotypes can be used in the invention. Examples of other AAV serotypes include, but not limited to, AAV-1, AAV-2, AAV-3, AAV4, AAV-5, AAVX7, and the like.

Control sequences can often be provided from commonly used promoters derived from viruses such as, polyoma, Adenovirus 2, cytomegalovirus and Simian Virus 40. Use of viral regulatory elements to direct expression of the protein can allow for high level constitutive expression of the protein in a variety of host cells. Ubiquitously expressing promoters can also be used include, for example, the early cytomegalovirus promoter Boshart et al. (1985) *Cell* 41:521-530, herpesvirus thymidine kinase (HSV-TK) promoter (McKnight et al. (1984) *Cell* 37: 253-262), β-actin promoters (e.g., the human β-actin promoter as described by Ng et al. (1985) *Mol. Cell Biol.* 5: 2720-2732) and colony stimulating factor-1 (CSF-1) promoter (Ladner et al. (1987) *EMBO J.* 6: 2693-2698). Alternatively, tissue-specific regulatory elements can be used, such as tissue specific promoters.

In another embodiment, the vector of the invention can be a virus other than the adeno-associated virus, which allows for expression of a nucleic acid molecule introduced into the viral nucleic acid. For example, replication defective retroviruses, adenoviruses and lentivirus can be used. Protocols for producing recombinant retroviruses and for infecting cells in vitro or in vivo with such viruses can be found in Current Protocols in Molecular Biology, Ausubel et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. The genome of adenovirus can be manipulated such that it encodes and expresses the protein of interest but is inactivated in terms of its ability to replicate in a normal lytic viral life cycle. See e.g., Berkner et al. (1988) *BioTechniques* 6:616; Rosenfelt et al. (1991) *Science* 252: 431434; and Rosenfeld et al. (1992) *Cell* 68:143-155. Suitable adenoviral vectors derived from the adenovirus strain Ad type 5 d1324 or other strains of adenovirus (e.g., Ad2, Ad3, Ad7 etc.) are well known to those skilled in the art.

Delivery systems include methods of in vitro, in vivo and ex vivo delivery of the antigen, antibody or antigen-binding portion. Generally, the antigen is delivered to the systemic circulatory system using methods known in the art. Preferred methods include peroral administration of the antigen. Other methods include intramuscular injection of the antigen, as discussed in section III. Antibodies can also be administered to the systemic system or directly to a targeted site in the region of the brain.

For in vivo delivery of antigen or antibodies or an antigen-binding portion, the antigen or antibody can be administered to a subject in a pharmaceutically acceptable carrier. The term "pharmaceutically acceptable carrier", as used herein, refers to any physiologically acceptable carrier for in vivo administration of the vectors of the present invention. Such carriers do not induce an immune response harmful to the individual receiving the composition, and are discussed in section III.

In one embodiment, antibody or antibody portion can be distributed throughout a wide region of the CNS, by injecting the antibody or antibody portion into the cerebrospinal fluid, e.g., by lumbar puncture (See e.g., Kapadia et al. (1996) *Neurosurg* 10: 585-587).

Alternatively, precise delivery of the antibody into specific sites of the brain, can be conducted using stereotactic microinjection techniques. For example, the subject being treated can be placed within a stereotactic frame base (MRI-compatible) and then imaged using high resolution MRI to determine the three-dimensional positioning of the particular region to be treated. The MRI images can then be transferred to a computer having the appropriate stereotactic software, and a number of images are used to determine a target site and trajectory for antibody microinjection. The software translates the trajectory into three-dimensional coordinates that are precisely registered for the stereotactic frame. In the case of intracranial delivery, the skull will be exposed, burr holes will be drilled above the entry site, and the stereotactic apparatus used to position the needle and ensure implantation at a predetermined depth. The antibody, or antibody portion can be delivered to regions, such as the cells of the spinal cord, brainstem, (medulla, pons, and midbrain), cerebellum, diencephalon (thalamus, hypothalamus), telencephalon (corpus stratium, cerebral cortex, or within the cortex, the occipital, temporal, parietal or frontal lobes), or combinations, thereof.

Alternatively, the antigen, antibody, or antibody portion, can be delivered using a non-viral delivery system. This includes delivery of the antigen or antibody or antibody portion to the desired tissues in colloidal dispersion systems that include, for example, macromolecule complexes, nanocapsules, microspheres, beads, and lipid-based systems including oil-in-water emulsions, micelles, mixed micelles, and liposomes.

Liposomes are artificial membrane vesicles which are useful as delivery vehicles in vitro and in vivo. In order for a liposome to be an efficient gene transfer vehicle, the following characteristics should be present: (1) encapsulation of the genetic material at high efficiency while not compromising the biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al. (1988) *Biotechniques,* 6:682). Examples of suitable lipids liposomes production include phosphatidyl compounds, such as phosphatidylglycerol, phosphatidylcholine, phosphatidylserine, phosphatidylethanolamine, sphingolipids, cerebrosides, and gangliosides. Additional examples of lipids include, but are not limited to, polylysine, protamine, sulfate and 3β-[N—(N', N' dimethylaminoethane) carbamoyl] cholesterol.

Alternatively, the antigen can be administered as a peptide vaccine. A synthetic peptide comprising an antigen binding region can be prepared using standard peptide synthesis method known in the art. It is often necessary to couple the peptide with a carrier. Exemplary and preferred carriers are keyhole limpet hemocyanin (KLH) and human serum albumin. Other carriers may include a variety of lymphokines and adjuvants such as INF, IL2, IL4, IL8 and others. Means for conjugating a peptide to a carrier protein are well known in the art and include glutaraldehyde, m-maleimidobenzoyl-N- hydroxysuccinimide ester, carbodiimyde and bis-biazotized benzidine. It is also understood that the peptide may be conjugated to a protein by genetic engineering techniques that are well known in the art. The preparation of vaccines which contain peptide sequences as active ingredients is generally well understood in the art. (See e.g., U.S. Pat. Nos. 4,608,251; 4,601,903; 4,599,231; 4,599,230; 4,596,792; and 4,578,770).

In one embodiment, particle-mediated delivery using a gene-gun can be used as a method to vaccinate a subject. Suitable particles for gene gun-based delivery of include gold particles which are coated with the DNA encoding the antigen. In one embodiment, the DNA encoding the antigen can be delivered as naked DNA without an expression vector. In another embodiment, the DNA encoding the antigen can be inserted into an expression plasmid. The antigen coated particles can be delivered into the epidermal layer of the skin to elicit an inflammatory response. Gene gun based delivery is described, for example by, Braun et al. (1999) *Virology* 265: 46-56; Drew et al. (1999) *Vaccine* 18:692-702; Degano et al. (1999) *Vaccine* 18:623-632; and Robinson (1999) *Int J Mol Med* 4:549-555; Lai et al. (1998) *Crit Rev Immunol* 18:449-84; See e.g., Accede et al. (1991) *Nature* 332: 815-818; and Wolff et al. (1990) *Science* 247:1465-1468 Murashatsu et al., (1998) *Int. J. Mol. Med.* 1: 55-62; Agracetus et al. (1996) *J. Biotechnol.* 26: 37-42; Johnson et al. (1993) *Genet. Eng.* 15: 225-236).

Expression of administered genes results in the induction of humoral and cellular immune responses against the encoded antigen. The nature of the immune response depends on the route, method, and timing of DNA delivery and can also be influenced by co-delivery of plasmids encoding immunomodulating cytokines like IFN-alpha, IL-2, or IL-12 and costimulatory molecules like B7-1 (See e.g., Tuting (1998) *J Invest Dermatol* 111: 183-188 and Barry et al. (1997) *Vaccine* 15:788-791). The method of DNA inoculation (gene gun versus intramuscular injection) and the form of the DNA-expressed antigen (cell-associated versus secreted) determine whether T-cell help will be primarily type 1 or type 2. Mechanistically, gene gun-delivered DNA initiates responses by transfected or antigen-bearing epidermal Langerhans cells that move in lymph from bombarded skin to the draining lymph nodes. Following intramuscular injections, the functional DNA appears to move as free DNA through blood to the spleen where professional antigen presenting cells initiate responses (Robinson et al. (1997) *Semin Immunol* 9:271-283).

Also within the scope of the invention is the delivery of the antigen in one or more combinations of the above delivery methods. For example, intradermal delivery of an antigen, followed by intramuscular injection of the antigen.

V Functional Genomics

Figure 5A:
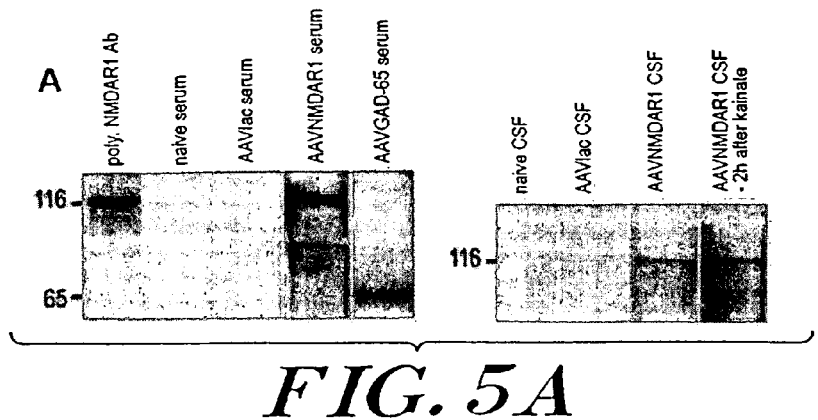
FIG. 5A is a photograph demonstrating antibody passage across an intact blood-brain barrier by immunoblot analysis of cerebrospinal fluid (CSF) from AAVlac, AAVNMDAR1 and AAVGAD vaccinated rats.

In another embodiment, the antigen, antibody or antibody portion of the invention can be used to modify the expression and/or secretion of one or more molecules (e.g., a neurotrophic factor, a neurotransmitter, or a neuroprotective agent), e.g., to enhance their neuroprotective capacity. For example, in order to provide neuroprotection in epilepsy or stroke, the NMDAR1 antigen can be administered to a subject to produce antibodies in the systemic circulatory system of the subject. The circulating anti-NMDAR1 antibodies migrate across the blood-brain barrier into the cerebrospinal fluid and bind to the NMDAR1 receptors in the cortex upon injury, disease or excessive neuronal activity. Migration of the antibodies into the cerebrospinal fluid as a result of kainate induced injury, is shown in FIG. 5A and in FIG. 10I. Example 6 demonstrates direct modulation of the NMDR receptor upon antibody binding. An indirect effect of antibody binding is also demonstrated based on monitoring Krox-24 expression. These binding of the anti-NMDAR1 to the NMDA receptors upregulates their expression, as demonstrated by the increase in their mRNA expression (See Example 6).

Accordingly, the invention also provides for methods of modifying the function of a target gene. The term "target protein" as used herein refers to a molecule to which an antibody binds and changes the function of. For example, the NMDA receptor to which the anti-NMDAR1 antibody binds, is a target protein. Modification of the target protein can, for example, increase, decrease, elevate or depress the secretion of certain molecules, for example, a neurotrophic factor, an altered expression of proteins (i.e. increase or decrease in protein expression) and modifications in the morphological and functional processes.

The invention also provides a method of introducing a new function to a target cell (e.g., a damaged neural cell) in a phenotypically useful way. A new function can be expressed in such defective target cells (e.g., damaged neural cells) by modifying the function of a target protein in/or on a cell. For example, by decreasing expression of the Knox-24 protein or by increasing the number of NMDA receptors (See example 3). Such modifications can result in a gain-of-function response, for example, improved learning and memory (See Example 7).

In one embodiment, modifications to cells using the methods of the invention includes the changes to the expression and/or secretion of a gene product. For example, to augment neurotransmitter function within the brain, such as, modifications to increase or decrease expression of choline acetyltransferase. Another example, includes modifications to produce tyrosine hydroxylase (an enzyme that coverts tyrosine to L-DOPA). The antigen or antibody of the invention can by used to increase the production of this enzyme and to continue to convert tyrosine to L-DOPA in the striatum. In a preferred embodiment, the modification can alter NMDA receptor numbers directly, or decrease Knox-24 protein expression (See Example 6). These modifications to the target gene can be used for functional genomic studies. For example, to modulate the effect of proteins and substances such as receptors (e.g. NMDA, GluR); neurotransmitters (e.g., dopamine, acetylcholine, serotonin, histamine and melatonin); transporters (e.g., EAAT); transcription factors, growth factors (e.g., epidermal growth factor, brain derived neurotrophic growth factor); ion channel proteins; and signal transduction molecules, as described in section I.

VI. Diseases

The brain, retina and testis are generally perceived as immune privileged sites as defined traditionally by the prolonged survival of allogeneic or xenogeneic tissue transplanted into these organs. Although it is now known that this immune privilege is relative and not absolute, many foreign antigens within the CNS escape immune surveillance and, moreover, self-antigens in the brain may not induce tolerance. Studies have shown that in paraneoplastic disorders (PND), circulating autoantibodies interact with neuronal antigens (Posner and Furneaux 1990. *Immunologic Mechanisms in Neurologic and Psychiatric Disease*, ed. Waksman, B. H., 187-219). It is believed that brain antigens previously sequestered from the immune system via the blood-brain barrier become presented to a naïve immune system when ectopically expressed in cancer cells and elicit a humoral immune response (Darnell, (1996) *Proc Natl Acad Sci USA,* 93:4529-4536).

Circulating plasma proteins and other large non-lipophilic molecules have very poor access to brain because of the impermeability of the cerebral endothelial tight junctions and astrocytic foot processes which constitute the blood-brain barrier (blood-brain barrier). Antigens within brain parenchyma generally undergo less immunosurveillance and antibodies circulating in the blood cross this barrier poorly under normal, basal conditions (Pollack and Lund (1990) *Exp. Neurol.* 108:114-121). There are examples which suggest that this immune privilege is relative, not absolute, and that the nervous system is not protected from antibody-mediated attack and protection. For example, the myasthenic syndrome of Lambert Eaton is associated with circulating antibodies which bind to nerve terminals, the principal target being the P/Q-type voltage-gated calcium channel (Kim and Neher (1988) *Science* 239:405-408). Circulating antibodies have also been described in Stiffnan syndrome (Solimena et al. (1988) *New England Journal of Medicine* 318:1012-1020) and Rasmussen's Disease (Rogers et al. (1994) *Science* 265:648-651). It is established that antibodies pass the blood-brain barrier poorly (Pollack and Lund (1990) *Exp. Neurol* 108:114-121), however, the blood-brain barrier is compromised after insults to the brain, including trauma, seizures, stroke or infection, allowing penetration of plasma molecules, including antibodies, into brain parenchyma.

While not required to provide a mechanism of action, the genetic vaccine of the invention may provide neuroprotective effects when the integrity of the blood-brain barrier is compromised (e.g., due to insult or injury to the brain, disease or excessive neuronal activity). The compromise in the blood-brain barrier enables a breach of the immune privilege of the brain and passage of antibodies to the targeted neurons resulting in the characteristic disease phenotype. Accordingly, the invention features a method of treating neurological disorders by vaccinating against selected brain antigens to induce a state of autoimmunity. An immune response to a brain self-antigen can be induced which, instead of having disease-inducing activity, has a therapeutic efficacy. Examples 3 and 4 demonstrate the neuroprotective effect of a vaccine comprising an NMDA receptor antigen that elicited the production of antibodies against the NMDA receptor. The genetic vaccine of the invention can be used to induce a high titer of circulating NMDA receptor autoantibodies which have minimal CNS penetration under resting, basal conditions. However, following an insult, injury, disease or excessive neuronal activity, to the brain and compromise of the blood-brain barrier, these antibodies pass into the brain more efficiently, bind to and interfere with the function of the NMDA receptor, thereby attenuating NMDA receptor-mediated injury.

In one embodiment, the invention provides a method for inhibiting NMDA activity in a subject suffering from a disorder in which NMDA receptor activity is detrimental. The NMDA receptor has been implicated in the pathophysiology of a wide variety of disorders. The invention provides methods for modulating NMDA activity in a subject suffering from such a disorder, which method comprises administering to the subject an antigen, antibody or antibody portion, such that NMDA receptor activity in the subject is modulated. Preferably, the subject is a human subject.

A disorder in which NMDA receptor activity is detrimental is a disorder in which modulation of NMDA receptor activity is expected to alleviate the symptoms and/or progression of the disorder. Antigens, antibodies, or antibody portions can be introduced into a subject in an amount suitable to ameliorate, reduce, alleviate or aid in, or at least partially correct a neurological disorder. Alleviation of the disorders may be evidenced, for example, by the neuroprotective effect of the antibody or antibody binding portion on regions of the brain (See Example 3 for neuroprotection against epilepsy and Example 4, for neuroprotection against stroke, and by the behavioral test described in Example 1).

There are numerous examples of disorders in which NMDA receptor activity can be detrimental. Neurological disorders to be treated by the invention include, but are not limited to, epilepsy, stroke, Parkinson's disease, Alzheimer's and other disorders in which the disease process is in part mediated by a brain protein or where a molecule binding to a brain protein would alter the disease phenotype, for example proteins involved in the signal transduction of neurotransmitters including receptors and ion channels, or the synthesis of neurotransmitters or the uptake and transport of brain chemicals. Representative examples of neurotransmitter receptors include, but are not limited to, the NMDA, AMPA and kainate receptors, dopamine, serotonin and noradrenergic receptors and transporters and neuropeptide receptors including the neurokinin-1 (NK1) receptor. Representative examples of transmitters include, but are not limited to, glutamate, GABA, dopamine, serotonin, acetylcholine, norepinephrine, adenosine, neuropeptide Y (NPY) and substance P. Representative examples of proteins that are important to neurological disorder include, but are not limited to, amyloid protein (AP) and amyloid precursor protein (APP) as well as the CAG repeat protein, huntington.

In one embodiment, the antigens, or antibodies or antibody portion thereof, can be used in therapy to treat the diseases or disorders described herein. In another embodiment, the antigen, antibodies or antibody portions thereof, can be used for the manufacture of a medicine for treating the diseases or disorders described herein. The use of the antigens, antibodies and antibody portions of the invention in the treatment of a few non-limiting specific disorders is discussed further below:

Stroke

In a preferred embodiment, the neurological disorder is stroke. A vaccine compositions comprising antigens of the NMDA receptor, in particular, antigens to NMDAR1 subunit, can be used to generate antibodies in the systemic circulation of a subject, as described in detail Example 3. The circulating antibodies penetrate the blood-brain barrier to provide a neuroprotective effect against stroke.

Epilepsy

In another preferred embodiment, the neurological disorder is epilepsy. In the case of epilepsy, there are both rat and monkey models in which effective therapies are predictive of therapeutic efficacy in humans. For example, rats which exhibit audiogenic seizures are commercially available. Example 4 demonstrates in detail the neuroprotective effect of the AAVNMDAR1 vaccine against seizures in the kainate epilepsy model. Antigen, antibodies or antibody portions of the invention can be introduced into the systemic circulation of these animals and seizures initiated. The neuroprotective capacity of the vaccine was determined by monitoring the onset, or decrease in seizure occurrence by EEG. FIG. 4 shows the reduction in epileptic seizures in animals vaccinated with the AAVNMDAR1 vaccine of the invention.

Huntington's Disease

The antigen or antibody or antibody portion can be used to treat neurological disorders resulting from neurodegeneration, such as that which occurs in human subjects with Huntington's disease. Models of neurodegenerative diseases in several different animals have been developed. For example, rat (Isacson et al. (1985) *Neuroscience* 16:799-817), monkey (Kanazawa, et al. (1986) Neurosci. Lett. 71:241-246), and baboon (Hantraye. et al. (1992) *Proc. Natl. Acad. Sci. USA* 89:4187-4191; Hantraye, et al. (1990) *Exp. Neurol.* 108:91-014; Isacson, et al. (1989) *Exp. Brain Res.* 75(1):213-220)

models of Huntington's disease have been described in which effective therapies are predictive of therapeutic efficacy in humans. Neurodegeneration in Huntington's disease typically involves degeneration in one or both nuclei forming the stratium or corpus stratium, the caudate nucleus and putamen. Administration of the antigen to the systemic circulatory system may result in antibodies to specific receptors or proteins in these regions. These antibodies may enter the central nervous system upon injury due to neurodegeneration in these regions and bind to a target gene to offer neuroprotection. Alternatively, antibodies or antibody portions generated in a mammal can be introduced into the systemic circulatory system, or to specific affected brain regions.

To assess therapeutic strategies, the antigen or antibody of the invention can be introduced into the animal model and a state resembling Huntington's diseases can be generated. Morphological and immunohistochemical studies can then be performed by conventional techniques to determine whether the antibody provided neuroprotection by assessing, both morphologically and functionally of the tissue. Behavioral tests can also be performed using standard techniques (See Example 1).

Parkinson's Disease

Parkinson's disease in humans primarily affects subcortical structures, especially the substantia nigra and loercus caeruleus. It is characterized by the loss of dopamine neurons in the substantia nigra, which have the basal ganglia as their major target organ. Several animal models of Parkinson's disease have been generated in which effective therapies are indicative of therapeutic efficacy in humans. These animal models include three rat models (the rats having lesions in substantia nigral dopaminergic cells caused by treatment with 6-hydroxydopamine, 1-methyl-4-phenyl-1,2,3,6-tetrahydropyridine (MPTP), or surgical transection of the nigral striatal pathway) (See, e.g. Björklund et al. (1982) *Nature* 298:652-654), a rhesus monkey model (the monkeys having lesions in substantia nigral dopaminergic cells caused by treatment with MPTP) (See, e.g., Smith, et al. (1993) *Neuroscience* 52):7-16; Bakay et al. (1985) *Appl. Neurophysiol.* 48:358-361; Zamir. et al. (1984) *Brain Res.* 322:356-360), and a sheep model (the sheep having lesions in substantia nigral dopaminergic cells caused by treatment with MPTP) (Baskin, et al. (1994) *Life Sci.* 54:471-479). In another embodiment, the antigen, antibody or antibody portion of the invention can be used to treat a subject with Parkinson's disease. To assess therapeutic strategies, morphological and immunohistochemical studies can be performed by conventional techniques. Behavioral tests can also be performed (See Example 1).

Amyloid Lateral Sclerosis (ALS)

Several models of amyloid lateral sclerosis are available. Mutations in the superoxide dismutase gene 1 (SOD-1) are found in patients with familial amyotrophic lateral sclerosis (FALS). Overexpression of a mutated human SOD-1 gene in mice results in neurodegenerative disease as result of motor neuron loss in lumbar spinal cord, providing a suitable model for FALS (See e.g., Mohajeri et al. (1998) *Exp Neurol* 150: 329-336). Transgenic models of ALS are also described (See e.g., Gurney (1997) *J Neurol Sci* 152:S67-73). Expression of mutant SOD1 genes in transgenic mice causes a progressive paralytic disease whose general features resemble ALS in humans. These models can be used to examine the effect of an antigen, antibody or antibody portion that can be used to modify the function of receptors or transporter proteins associated with ALS (e.g., EAAT2 transporter protein). A gain-of-function in these models can monitored, for example, improvement in motor impairments of the animal's limbs.

Neuronal activation has also been associated with a number of neuroendocrine systems. Different regions of the brain activate different neuroendocrine systems (Hoffman et al. (1993) *Front Neurendocrinol.* 14: 173-213) and physiological response injury (Dubner et al. (1992) *Trends Neurosci.* 15: 96-103). Accordingly, the invention also provides methods and compositions of treating neuroendocrine disorders, for example, obesity and diabetes mellitus.

Obesity

The antigen, antibodies or antibody portions can also be used to treat or modify obesity in a subject. Mouse models for obesity are known in that art, for example, obese-diabetic mice (ob/ob), and obese-diabetic (db/db) mice from the Jackson Laboratories (Bar Harbor, Me.). (See e.g., Collins et al. (1996) *J Biol Chem* 271:9437-9440; Darling (1996) *Curr Opin Genet Dev* 6:289-294; Andersson (1996) *Ann. Med.* 28:5-7; leptin (Van Heek et al. (1997) *J. Clin. Invest* 99:385-390). These animal models can be used to assess the effect of an antigen, antibody or antibody portion on weight gain by modifying the function of neurotransmitters.

The hypothalamus plays a significant role in obesity, particularly in regulating neuropeptide Y (NPY), a 36 amino acid peptide secreted by hypothalamic neurons and a potent substance that stimulates appetite. NPY belongs to a family of neuroendocrine peptides including pancreatic polypeptide and peptide YY. The amino acid sequence of NPY and the location of NPY-expressing neurons within the brain are described in Larhammar, (1996) *Regulatory Peptides*, 62: 1-11. NPY is observed in the hypothalamus of obese animals (Sanacora et al., (1990) *Endocrinol.* 127:730-737; Sanacora et al. (1990) *J Neuroendocrinol.*, 4:353-357). Secretion of NPY from neurons within the hypothalamus stimulates feeding and chronically high levels of NPY expression result in hyperphagia and obesity. The ability to reduce high levels of NPY results in the diminution of the drive to eat. NPY gene regulation and physiology are reviewed in Berelowitz et al. (1992) *TEM* 3:127-133.

Growth hormone releasing factor (GRF), is another example of a peptide present in high concentration in the hypothalamus. GRF is the primary stimulatory factor controlling synthesis and secretion of pituitary growth hormone (GH), a critical regulatory hormone of metabolic homeostasis controlling breakdown of fat (lipolysis) and synthesis of protein. The antigen, antibody or antibody portion can be used regulate, the expression of neurotransmitters such as neuropeptide Y. Examples of other neurotransmitters involved in feeding and metabolism include, galanin, norepinephrine, dopamine, and β-endorphin release. Additional examples include, but are not limited to, cocaine- and amphetamine-regulated transcript (CART), orexin, thyrotropin-releasing hormone (TRH), leptin, corticotropin-releasing hormone (CRH) and pro-opiomelanocortin (POMC). The antigen, antibody or antibody portion can also be used to modify the receptors of these neurotransmitters.

Diabetes

A summary of insulin-dependent diabetes mellitus and its animal models is described by Wong et al. (1999) *Curr Opin Immunol* 11:643-647. These models can be used to investigate the effect of an antigen, antibody or antibody portion on diabetes in a animal. A few autoantigens have been associated with Type I diabetes mellitus, for example, insulin (Palmer et al. (1983) *Science* 222:1337-1339), glutamic acid decarboxylase (GAD) (Baekkeskov et al. (1990) *Nature* 347:151-156) and carboxypeptidase H (Castano. et al. (1991) *J. Clin. Endocr. Metab,* 73:1197-1201), and the glycolipids GT3 (Gillard, et al. (1989) *Journal Immunol. Methods* 142:3826-3832) and GM2-1 (Dotta, et al. (1992) *Endocrinology* 130: 37-42) and PM-1 (U.S. Pat. No. 5,908,627). The methods of the invention to treat or prevent the development of Type I diabetes by modulating these proteins.

Reproduction

Substances involved in reproduction can also be modified by using antigen, antibodies, or antibody portions to modify the function of these substances. Suitable animal models for reproduction are Sprague-Dawley rats, which are readily available. For example, modifying the function of luteinizing hormone-releasing hormone (LHRH), a hormone regulated by the hypothalamus and involved in the stimulation of ovulation and uterine growth (Fueshko et al. (1994) *Dev Biol* 166:331-348; Hahn et al. (1984) *Endocr Res*, 10: 123-138). Luteinizing hormone-releasing hormone also plays a role in male sterility by inhibiting the action of luteinizing hormone-releasing hormone with a synthetic decapeptide (Carelli (1982) *Proc Natl. Acad. Sci. USA* 79:5392-5395).

Another substance with a role in reproduction is colony-stimulating factor-1 and the CSF-1 null mouse model can be used to study the biological functions of CSF-1. CSF-1 is a neurotrophic factor acting through the microglia and the absence of CSF-1 results in severe electro-physiological abnormalities in the cortex (Pollard (1997) *Mol Reprod Dev* 46:54-60). A role for CSF-1 in reproduction was originally suggested by the sex steroid hormone-regulated uterine epithelial synthesis of CSF-1 and the expression of its receptor in trophoblast and decidual cells. CSF-1 also show that it functions in male fertility.

The method of the invention can be used to treat disorders, such as mania, anxiety, depression and psychosis (See PCT Nos. WO 95/16679, WO 95/18124 and WO 95/23798). Neurokinin-1 (NK-1) receptor plays a significant role in these disorders. Neurokinin-1 antagonists are being developed for the treatment of a number of physiological disorders associated with an excess or imbalance of tachykinins, and in particular substance P. The method of the invention can also be used to produce antibodies against NK-1 to treat bipolar disorders.

Depression

The antigen, antibodies or antibody portions can also be used to treat or alleviate depression. A well known animal model for depression is the Porsolt's swim test model (Porsolt, (1979) *Biomedicine* 30:139-140). This model investigates the behavior of rats or mice when forced to swim in a restricted space and the attempts of the animals to escape and become immobile. The immobile state reflects the state of lowered mood in the animal. This model can be used to investigate the effect an antigen, antibody or antigen on neuropeptides, neurotransmitters and receptors involved in depression, for example, NK-1, the effect of brain histamine and histamine receptors (Lamberti et al. (1998) *Br J Pharmacol* 123:1331-1336).

The present invention is further illustrated by the following examples which in now way should be construed as being further limiting. The contents of all cited references a (including literature references, issued patents, published patent applications and co-pending applications) cited throughout this application are hereby expressly incorporated by reference in their entirety.

EXAMPLES

Example 1

Methods and Materials (A) Vector Construction

A full length mouse NMDAR1 cDNA was subcloned into the AAV plasmid from the parent plasmid, pSub201 under the control of a CMV immediate-early promoter and bovine growth hormone (bGH) polyadenylation site between the AAV inverted terminal repeats, as previously described (During et al. (1998) *Nature Med.* 4:1131-1135). Recombinant AAVNMDAR1 virus was generated using the helper-free packaging system as described by During et al. (1998), supra. Alternatively, the full length mouse cDNA can be subcloned into the AAV plasmid in a similar manner. The detailed discussion that follows is to the NMDAR1 receptor, although comparative results can be obtained with the Glu R receptor.

(B) Peroral Administration

Male Wistar rats (300-350 g) were obtained from the Animal Resources Unit, Univ. of Auckland and studies approved by the Animal Ethics Committee. Rats were fasted overnight with access to water only before being anaesthetized with ketamine/xylazine (60 mg/6 mg; per kg i.p.) and vector (AAVNMDAR1 or control AAVlac) diluted in PBS to $1\times10^9$ infectious units in a final volume of 120 µl, was administered via an orogastric tube. Rats were allowed to recover and were returned to standard rat chow 20 h after vector administration.

(C) PCR Amplification and Genomic DNA

Eight months after viral administration, animals were sacrificed and genomic DNA was extracted from gut, testes, spleen and liver using standard methods. 200 ng DNA, 400 nM of CMV primers, CMV-1 (5' CCCAGTACATGACCT-TATGGG 3') (SEQ ID NO: 1) and CMV-2 (5' GGAGACT-TGGAAATCCCCGT 3') (SEQ ID NO: 2) were used in conjunction with the PCR master kit (Boehringer Mannheim) to amplify a 141 bp product. The cycling parameters were 5 min at 94° C. followed by 40 cycles of 1 min at 94° C., 30 sec at 49° C., 30 sec at 72° C. Analysis of β-actin genomic DNA was used to monitor DNA integrity. β-actin primers β-A1 (5' CTCTTCCAGCCTTCCTTCC 3') (SEQ ID NO: 3) and β-A2 (5' GTCACCTTCACCGTTCCAG 3') (SEQ ID NO: 4) were used to amplify a 772 bp band. After amplification, 5 ml of PCR products were electrophoresed on a 2% agarose gel containing ethidium bromide and visualized under UV.

(D) IgG Isolation and Purification

Total IgG from AAVNMDAR1, AAVlac and naïve serum was isolated using an ImmunoPure (G) IgG Purification Kit (Pierce, Rockford, EL). After acid elution, the IgG fractions were neutralized and dialysed against PBS. SDS-PAGE analysis confirmed purity of the sample. Any contaminating albumin was removed using affigel blue Biorad). The final purity of each IgG sample was >98%. To ensure the immunoreactive species had been successfully isolated, each AAVNMDAR1 IgG preparation was screened for anti-NMDAR1 activity.

(E) Primary Neuronal Cultures

Pregnant Wistar rats were overdosed with pentobarbital under aspectic conditions, and the midbrain region was dissected from E15 embryos into warm dissecting medium ($Ca^{2+}$ and $Mg^{2+}$-free Hank's balanced salt solution containing 0.6% glucose, 100 U/ml penicillin, 100 mg/ml streptomycin, 15 mM HEPES; Gibco BRL). Tissue was digested in 0.25% trypsin (Gibco BRL) containing 200 µg/ml DNase (Sigma) in dissecting medium for 15 min at 37° C. in a shaking waterbath. Trypsin digestion was terminated by the addition of trypsin inhibition medium (100 µg/ml soybean trypsin inhibitor (Sigma), 20% FCS (Gibco BRL), 200 µg/ml DNase in dissecting medium), and the tissue washed twice in dissecting medium containing 10% FCS and 200 µg/ml DNase. A cell suspension was obtained by tissue trituration and filtration through a 100 gm nylon filter. Cells were pelleted at 400 g, resuspended and plated onto poly-1-lysine-coated coverslips at a density of 250,000 cells/$cm^2$ in NEUROBASAL™ basal medium containing B27 supplement and 0.5 mM L-glutamine (all from Gibco BRL). Medium was replenished every 48 h, with the addition of a mitotic inhibitor (0.5 μM cytosine arabinoside) after 4 days. Cultures were grown for at least 9 days prior to calcium imaging.

(F) MTT Assay

Cells were plated out in 96-well plates as above. Antibody-treated cells were incubated in purified IgG fraction for 16 hours prior to addition of NMDA medium for a further 22 hours before addition of 20 ml of 5 mg/ml MTT (Sigma M2128) in PBS to each well for 2 hours at which time purple crystals were readily apparent in the cells. 10% SDS in 0.01 M HCl was added and left overnight to break up the cells. Absorbance was then read at 595 nm on an ELISA plate reader.

(G) Immunohistochemistry and Autoradiography

Four weeks or 5 months after vector administration, rats were overdosed with pentobarbital. The gastrointestinal tract was fixed in 4% paraformaldehyde in 0.1 M phosphate buffer (pH 7.4) overnight, followed by cryoprotection in 30% sucrose in PBS. For the gut cell marker immunohistochemistry, representative portions of the gut were freshly frozen. Twenty micron sections from the proximal intestine were cut on a cryostat and thaw mounted onto poly-lysine coated slides. Immunohistochemistry using a monoclonal NMDAR1 antibody (1:250 dilution, Chemicon) and propidium iodide staining was conducted as described previously (During et al. (1998) *Nature Med.* 4: 1131).

For gut cell markers, double label immunohistochemistry was performed using monoclonal antibodies to SIRP (1:50, Chemicon) and dendritic cells (1:5, Chemicon), followed by a unlabelled secondary anti-mouse IgG blocking step prior to NMDAR1 immunohistochemistry, with detection using secondary anti-mouse antibodies conjugated with Cy3 or Cy5 (1:250, Jackson Immunoresearch). Immediately prior to confocal imaging, sections were incubated with acridine orange (0.01% in PBS, pH 6.2) for 1 min, washed in PBS and mounted in Vectashield (Vector).

Brain immunohistochemistry was performed as described previously on slide-mounted sections (Young et al. (1999), *Nature Med.* 5: 448). Following fixation and washing, sections were incubated overnight at room temperature with a rabbit antibody to clusterin (1:200 provided by D. Christie, University of Auckland) diluted in PBS-Triton containing 1% normal goat serum and 0.4 mg/ml thiomersal. Sections were washed before application of secondary anti-rabbit FITC (Jackson Immunoresearch) followed by NeuN (1:1000, Chemicon) immunohistochemistry and detection with a secondary anti-mouse Cy3 conjugated antibody (Jackson Immunoresearch). Immunofluorescent signals were captured using a Leica 4d TCS confocal microscope and all images processed using Adobe Photoshop 4.0 (Adobe Systems). Immunohistochemistry with a commercial NMDAR1 antibody (Chemicon) and naïve, AAVlac or AAVNMDAR1 purified IgG at a concentration of 50 μg/ml was conducted on sections from naïve rats that had been perfused with PBS. Sections were washed before application of biotinylated secondary goat anti-rabbit or rat antibodies (1:250; Sigma) followed by ExtrAvidin peroxidase (1:250; Sigma) incubation and DAB visualisation (young et al (1999) supra). Peroxidase-conjugated Isolectin-B4 (1:50, Sigma) was applied to fixed sections followed by DAB visualisation.

(H) TUNEL Staining

TUNEL staining was performed prior to NeuN immunohistochemistry on 16 μm frozen coronal hippocampal brain sections as described previously (44) with the following modifications. After fixation and washing, sections were pre-incubated with 100 μl TdT buffer (Gibco BRL) for 10 min at RT followed by a 1 h incubation in a reaction mixture containing 0.75 μl biotin 14-dATP (Gibco BRL), 0.75 μl TdT (Gibco BRL), 15 μl 5×TdT buffer and 58.5 μl distilled water at 37° C. After the 2×SSC rinse and incubation with 2% BSA in PBS-Triton, sections were incubated with 200 μL ExtrAvidin-FITC (1:100, Sigma) for 1 h. Negative and positive controls were conducted as described previously by Young et al (1999) supra.

(I) Calcium Imaging

Primary mescephalic neurons were incubated for 16 h with the purified IgG at a concentration of 50 μg/ml prior to loading with 2 μM Oregon Green 488 BAPTA-1 (Molecular Probes) for 30 min followed by a HEPES-buffered saline washes. Confocal images were collected using a Leica 4d TCS confocal microscope at 4 sec intervals before cells were challenged with 100 pM NMDA (in $Mg^{2+}$-free solution containing 3 μM glycine). The images were pseudocoloured according to fluorescent intensity, with red representing basal $Ca^{2+}$ levels and yellow representing higher $Ca^{2+}$ concentrations. Changes in fluorescent signal were assessed by measuring fluorescent intensity in cells relative to basal levels using NIH image (NIM and expressed as a ratio of fluorescent intensity following NMDA challenge over basal levels.

(J) Immunoblots

For β-galactosidase antibody screening, 1 μg purified β-galactosidase protein (Sigma) was separated on a 10% acrylamide gel under reducing conditions and transferred to a nitrocellulose membrane. Serum samples from AAVNMDAR1, naïve and AAVlac animals (1:200), or monoclonal β-galactosidase (1:5000, Gibco BRL) were applied for 1 h at room temperature (RT) or overnight at 4° C. following a 90 min incubation in Tris-buffered saline containing 0.1% Tween 20 (TBST) containing 5% fetal calf serum (FCS) to block non-specific binding. Bound antibodies were detected using a peroxidase-labeled anti-rat or mouse antibody (1:12,000, Sigma) for 1 h at RT, and visualized using the ECL detection system (Amersham). Hippocampal and cortical extracts were prepared from naïve rat brain. Two preparations were used: (i) a crude hippocampal or cortex extract was prepared by homogenizing the tissue in ice cold 320 mM sucrose in 10 mM Tris-HCl, pH 7.4; (ii) a non-denatured membrane extract was prepared by homogenizing tissue as described above, in the presence of protease inhibitors (MINI COMPLETE™, protease inhibitor Boehringer Mannheim). Following centrifugation at 7000 g, 10 min, 4° C., the resulting supernatant was centrifuged at 37,000 g, 40 min, 4° C. and the pellet resuspended in 10 mM Tris-HCl, pH 7.4 containing protease inhibitors. For NMDAR1 antibody screening, 20 μg total hippocampal extract was separated on a 12% reducing gel or 20 μg non-denatured hippocampal membrane protein on a 10% reducing gel, transferred to nitrocellulose, and blocked. As above, serum (1:200) was screened along with a monoclonal NMDAR1 (1:3000, Chemicon MAB363) and/or a polyclonal NMDAR1 (1:250, Chemicon AB1516) antibody, and the bound antibodies detected as described above. AAV-GAD65 serum (1:200) and commercial GAD65 antibody (Chemicon) was screened against 20 mg of a hippocampal cytosolic fraction, with detection as above. Naïve, AAVlac or AAVNMDAR1 CSF (1:5 dilution) was screened against 30 μg of a hippocampal extract and the ECL plus (Amersham) detection system used.

(K) Peptide Preparation and Epitope Mapping.

Ninety-four sequential biotinylated peptides overlapping by 6 residues were synthesised (Chiron Technologies, Australia). 1.2 mmol of each peptide was reconstituted in 0.2 ml DMSO and stored as stock solutions at −20° C. Prior to use, the peptides were diluted 1:1000 in phosphate-buffered saline containing 0.1% Tween 20 (PBST). Plates were coated with streptavidin (5 mg/ml) at 37° C. overnight and then blocked for 2 h at RT with 1% FCS/PBST. Diluted peptides were added and incubated for 2 h at RT. Serum from AAVNMDAR1, AAVlac and naïve rats was then added (diluted 1:200) and incubated at 4° C. overnight. To detect bound IgG, peroxidase-conjugated anti-rat secondary antibody (1:40,000) was added, and after 1 h at RT, OPD substrate (Sigma) was applied and absorption at 490 nm determined. To determine the specificity of the NMDAR1 sera for each peptide, the ratio between the AAVNMDAR1 signal (absorbance at 490 nm; peptide ELISA) and mean AAVlac signals was calculated. The final values were plotted to produce the epitope maps shown in FIGS. 3D-H.

(L) Kainic Acid Administration

Three weeks following vector, animals were anaesthetised with 60 mg/kg i.p. pentobarbital and implanted with bipolar recording electrodes (MS33-2B, Plastics One Inc.) into the right dorsal hippocampus under stereotaxic guidance ((anterior posterior (AP) −3.3 mm, medial-lateral (ML) 2.0 mm, dorsal-ventral (DV) 3.6 mm, bregma=0). One week later, rats received 10 mg/kg kainate i.p. and seizures were monitored on a Grass 79E EEG recorder. After 45 min of seizure activity, animals were administered an anticonvulsant dose of pentobarbital (30 mg/kg i.p.). Animals were sacrificed 3 days after kainate injection. Following pentobarbital anaesthesia, brains were removed and snap-frozen on dry ice. Coronal hippocampal sections (16 µm) were taken for TUNEL and clusterin analysis.

(M) Middle Cerebral Artery Occlusion (MCAO)

Five months after vector administration, endothelin-1 (60 pmol in 3 µl saline; Novabiochem) was injected via a 30 g cannula above the middle cerebral artery (AP+0.2 mm, ML 5.9 mm, DV from dura 7.5 mm) of anaesthetised animals (Darnell (1996) *Proc Natl Acad Sci USA* 93: 4529). Following recovery from surgery, animals were sacrificed 3 days later. Brains were removed, frozen and 20 µm coronal sections taken for haematoxylin-eosin staining and isolectin B4 analysis. Infarct volume estimates were determined on serial haematoxylin-eosin stained sections using the Cavalieri method (Gundersen et al. (1988) *APMIS* 96: 857).

(N) IgG Penetration

To investigate basal and kainate-induced IgG penetration, vaccinated animals (naïve n=4, AAVlac n=4, AAVNMDAR1 n=4) and AAVNMDAR1 animals 90 min after kainate administration (Young et al. (1999) Nat. Med. 5: 448-453) (n=2) were anaesthetised before perfusion with PBS to remove endogenous IgG present in blood vessels. The brains were removed and frozen on dry ice before 16 µm coronal sections at the level of the hippocampus were taken for anti-rat IgG (1:250, Sigma) immunohistochemistry.

(O) $^3$H-MK-801 Autoradiography

Hippocampal sections were incubated in 50 mM Tris HCl containing 2.5 mM $CaCl_2$, pH 7.4 for 1 h and dried before being incubated with 20 nM $^3$H-MK-801 (NEN) for 1 h. Non-specific binding was determined by labelling in the presence of 100 µM cold MK-801. Sections were rinsed twice in ice-cold Tris HCl buffer for 1 min each, followed by a quick dip in ice-cold distilled water and were dried overnight at 4° C. before being exposed against $^3$H-Hyperfilm (Amersham) for 3 weeks. Density measurements were made from autoradiograms using NIH image. Statistical analysis was conducted using Student's t-test.

(P) In Situ Hybridization

In situ hybridization was performed on 16 Pin frozen hippocampal sections from AAVlac and AAVNMDAR1-vaccinated animals using oligonucleotide probes to NMDAR1 (5' CAC AGC CTG GAT GGC CTC AGC TGC GCT CTC GTA ATT GTG TTT T 3') (SEQ ID NO: 5), NMDAR2A (5' AGA AGG CCC GTG GGA GCT TTC CCT TTG GCT AAG TTT C3') (SEQ ID NO: 6), NMDAR213 (5' CAT GTT CTT CTT GGC CGT GCG GAG CAA GCG TAG GAT GTT GGA GTG GGT 3') (SEQ ID NO: 7) and trkB as described previously (Young et al. (1999) Nat. Med. 5: 448-453). Density measurements were conducted on film autoradiograms as described above for H-MK-801 binding.

(Q) Cerebrospinal Fluid (CSF) Sampling

A subgroup of animals were anaesthetised with 60 mg/kg i.p. pentobarbital and a non-traumatic sample of CSF (80-100 µl) was obtained from the cisterna magna using a 27 g needle. Rats were left at least 7 days following CSF sampling before kainate injection (10 mg/kg i.p). Ninety min later, rats were anaesthetised as described above and CSF sampled.

(R) Behavioural Tests (i) Barnes Circular Maze—This was carried out as described previously (Barnes et al. (1979) *J. Comp. Physiol. Psychol.* 93: 74-104). Briefly, rats use spatial navigation to escape from a brightly-lit elevated circular 2 m diameter table which has 18 equally spaced holes around the circumference, one hole which leads to an escape box. On the first day of testing, each rat was placed in the escape box for a four min adaptation period. After one min in the home cage, trial 1 began. On subsequent days, two trials were conducted, separated by one min in the home cage. Testing continued for six days, (11 trials in all). For each trial, rats were placed in the centre of the table under a cylindrical start box for 30 sec, then allowed four min to find and enter the escape tunnel. During this time, the number of incorrect holes searched and latency to enter the tunnel were recorded. All animals spent one min in the tunnel at the conclusion of their trials. Between trials, the table was cleaned with 70% ethanol, and the hole under which the tunnel was placed, though always in the same spatial location, was randomly determined for each rat. From trial 8 onwards, the position of the escape box was altered by 135 degrees, to control for the possibility that rats had learnt to navigate to the escape box by other than spatial means.

(ii) Line crossing mobility test—A 2 meter diameter circular table was divided into 9 segments of approximately equal size. Each rat was placed in the centre of the table, and allowed 5 min of free movement during which a record was made of the number of times the rat's two front feet crossed a line separating two segments. Testing was conducted for 5 days, (1 trial per day). Between trials the table surface was cleaned with 70% ethanol.

(iii) Circular track mobility test—The track used was a modified version of one used to test mobility in mice. Each rat was placed inside the track at the start position, facing clockwise, and the number of circuits completed in 5 min was recorded. This procedure was conducted for 5 days.

(iv) Contextual Fear Conditioning—Each rat was placed in a metal operant chamber (Med Associates Inc.) for 2.5 min of exploration. A tone was then sounded for 30 sec, with a 0.4 mA shock administered during the last 2 sec. 1 h later, rats were returned to the chamber, and scored for the number of 5 sec intervals spent frozen over a 5 min period. Results were analyzed with Systat v5.2. (Systat). Two way ANOVA tests were used, with rat type as the explanatory variable, and day and time (first or second trial of day) as repeated measures where appropriate. Individual trials were analyzed using a Wilcoxon Rank Sum or two-tailed independent t-test.

(S) Nociception Pain Test

The hot plate and tail-immersion tests were performed to assess the effects of vaccinations on nociception. The hot plate test was performed by placing the rat on an aluminum plate maintained at 55° C. (Barnstead Thermolyne Co.) and measuring the latency in detecting a nociceptive response identified as a licking of a hindpaw or an escape response (jumping over a 20 cm barrier). Any rat that did not respond within 15 sec would have been removed from the hot plate, but all rats responded within 10 sec. The tail immersion test was performed by wrapping the rat in a towel then immersing the tail in a beaker of water kept at a constant 55° C. temperature. The latency for the animal to either remove the tail or elicit a jerk response was measured. Any rat not responding within 15 sec would immediately be removed from the water, however all tested rats responded within 10 sec. All behavioural tests were carried out by blinded investigators.

Example 2

Immunization of Animals with the AAVNMDR1 Genetic Vaccine

A full length mouse NMDAR1 cDNA was subcloned into an adeno-associated virus (AAV) plasmid and subsequently packaged and purified to yield a high titre recombinant AAV virus, AAVNMDAR1 (FIG. 1A and FIG. 1C). FIG. 1A shows the plasmid map of the NMDAR1 construct. FIG. 1C shows transduction of HEK 293 cells (arrows) by AAVNMDAR1 using NMDAR1 immunocytochemistry. This vector was administered via an orogastric tube into the stomach of a group of rats with a control group receiving a similar dose of a recombinant AAV virus expressing beta-galactosidase (AAVlac) (During et al. (1998) Nature Med. 4:1131-1135).

(i) Oral Genetic Vaccination with AAVNMDAR1

To demonstrate successful peroral administration of the vaccine and production of antibodies, genomic DNA and protein expression in the intestine was examined. Oral vaccines are usually scavenged by intestinal M cells, rapidly taken up by the antigen presenting cells (APC) in Peyers patches and the lamina propria, and can induce strong humoral immune responses (Shalby et al. (1995) Clin. Immunol. Immunopath 74:127).

FIG. 1B, is a photograph of an agarose gel showing PCR amplification of CMV promoter from genomic DNA extracted from AAVNMDAR1 and AAVlac-vaccinated rats. (Lane 1, kb plus DNA ladder; Lane 2, DNA extracted from the gut of an AAVNMDAR1 rat; Lane 3, DNA extracted from the gut of an AAVlac rat; Lane 4, DNA extracted from control naïve rat gut; Lane 5,6,7, show DNA extracted from the liver, spleen and testes respectively, of a AAVNMDAR1 rat; Lane 8, no template control; Lane 9, positive control (CMV promoter amplified from AAVNMDAR1 plasmid. Amplification of CMV with this set of primers generated a 141 bp product consistent with that found for the positive control and Lanes 2 and 3 (lower arrow). b-actin genomic DNA served as a control of DNA integrity (upper arrowhead).

The results show that in rats treated with the oral AAVNMDAR1 vector, transduction of intestinal cells was confirmed by PCR amplification of a portion of the CMV promoter from genomic DNA isolated from the proximal intestine. Similarly, the PCR product was also detected in AAVlac-immunized rat intestine, but not detected in DNA from the intestine of naïve rats, or in the liver, spleen or testis of any AAVNMDAR1- or AAVlac-immunized rats (FIG. 1B).

(ii) Protein Expression

The expression of NMDAR1 was determined. NMDAR1 protein expression in the intestine was detected at four weeks (FIGS. 1D-F) and five months (FIG. 1H) following peroral AAVNMDAR1 administration. Double immunofluorescence analysis with propidium iodide was used to show the lamina propria (lp) and epithelial (ep) cell layers. NMDAR1 immunohistochemistry showed NMDAR1 protein expressed within these two regions. NMDAR1 Protein expression was also determined using a commercially available NMDAR1 primary antibody and fluorescent secondary antibody as described in Example 1. NMDAR1 protein was not expressed in AAVlac-treated animals at 4 weeks (FIG. 1G) or 5 months (not shown).

Using confocal microscopy imaging, expression was observed primarily in the lamina propria as previously described for AAVlac-treated animals (During et al. (1998) Nature Med. 4: 1131). At a dose of $10^9$ rAAV infectious particles, a total of 9-12 million lamina propria cells were transduced at 4 weeks with approximately ~10 million immunoreactive cells remaining at 5 months with no loss of expression, as previously reported using E. coli lacZ as the transgene (During et al, supra). Double label immunofluorescent staining combined with acridine orange counterstaining (green) to visualise nuclei showed colocalisation of NMDAR1 protein in FIG. 2B and FIG. 2D with antibodies to gut cell markers (FIG. 2A) SIRP and (FIG. 2C) dendritic cells. These results showed that transduced cells were immunoreactive using the antibodies MRC OX-41 and OX-62 to define signal regulatory proteins expressed on cells of myeloid origin (SIRP) and dendritic cells respectively confirming the ectopic NMDAR1 expression in professional antigen-presenting cells.

(iii) Circulating Antibodies

To determine the presence of circulating NMDAR1 antibodies, blood was removed from the vaccinated animals and the serum analyzed for presence of specific antibodies. Sera (1:200) from AAVlac, AAVNMDAR1 and naïve control rats, were screened by immunoblot analysis for the presence of β-galactosidase antibodies. 1 μg purified β-galactosidase was loaded per lane (gel not shown). (Lane c, commercial β-galactosidase antibody; Lane 1, naïve control serum; Lane 2, AAVNMDAR1 serum 4 weeks after vaccination; Lane 3, AAVlac serum 4 weeks after vector administration; Lanes 4-5, AAVlac serum from two individual animals 4 months after vector). The results show that in AAVlac-treated animals, IgG antibodies were detected at 4 weeks with titres further increasing at 16 weeks. Using a purified beta-galactosidase enzyme preparation, a commercial monoclonal antibody recognized two molecular weight protein species of 116 and 85 kD on immunoblots. Some animals had antibodies that bound preferentially to the 85 kD species whereas other animals had serum antibodies with higher affinity to the 116 kD protein.

the results from serum (1:200) from AAVlac, AAVNMDAR1 and naïve control rats, screened by immunoblot analysis for the presence of NMDAR1 antibodies. 20 μg hippocampal membrane extract was loaded per lane. (Lane c, commercial NMDAR1 antibody (Chemicon, MAB363); Lane 1, naïve serum; Lane 2, AAVlac serum (4 weeks); Lane 3, AAVNMDAR1 serum (4 weeks); Lane 4, AAVNMDAR1 serum (4 months)). The results showed that immunoblotting of AAVNMDAR1 serum to a hippocampal membrane extract yielded the expected 117 kD band, consistent with the molecular weight of the native NMDAR1 receptor subunit and similarly recognized by commercial antibodies. The sera from naïve control (n=4) or AAVlac (n=12) immunized animals showed no binding to the brain extract.

Sera (1:200) were screened against a denatured hippocampal extract, 20 μg was loaded per lane. (Lane P, polyclonal NMDAR1 antibody (Chemicon AB1516); Lane M, monoclonal NMDAR1 antibody (Chemicon, MAB363); Lanes N35, N64, N52, is AAVNMDAR1 serum from three different animals showing specific affinities for different NMDAR1 breakdown products. (gel not shown) Brain extracts prepared under more severe denaturing conditions resulted in degradation of the native receptor as shown by detection with a commercial monoclonal antibody which bound fragments running at 32 kD and 67 kD. Of interest, individual AAVNMDAR1 rats showed different patterns of binding to some of these fragments (Lanes N35, N64 and N52). These data demonstrate that AAV can serve as an oral vaccine and that immunized animals generated antibodies against a range of NMDAR1 epitopes.

(iv) Epitope Mapping of NMDAR1

To further define the range of epitopes, a total of 94 overlapping 16 mers were synthesized covering the entire 938 amino acids of the native NMDAR1 protein as described in Example 1K. Serum from AAVNMDAR1, AAVlac and naïve rats were screened against this panel of 16 mers.

FIGS. 3A-3E of rats N11, N19, N21, N52, N64 show the epitope map profiles of five different AAVNMDAR1-treated animals. Specificity is measured as a ratio between the AAVNMDAR1 signal and mean AAVlac signals for each peptide. The results showed that none of the naïve (n=4) or AAVlac rats (n=14) screened had specific binding to any of the peptides. In contrast, AAVNMDAR1-immunized rats showed specific binding to peptides which corresponded to functional domains within the extracellular segments of the receptor. These included peptide 49 (amino acids 483-498) which represented the N-terminal side of M1, the first transmembrane domain (rat N19, FIG. 3B), and two peptides corresponding to the extracellular domain between M3 and M4, peptide 69 (amino acids 681-696; rat N21, FIG. 3C) and peptide 72 (amino acids 711-726; rat N64, FIG. 3E). Each of these three peptides contain critical residues for glycine binding (Kuryatov et al (1994) *Neuron* 12: 1291; Wafford et al. (1995) *Mol. Pharmacol.* 47: 374; Wood et al. (1997) *J. Biol. Chem.* 272: 3532). The most common pattern observed in serum from 7 of the 19 AAVNMDAR1 rats screened was specific binding to peptides adjacent to the M4n region (peptide 80, amino acids 791-807) and/or peptide 65 (amino acids 641-657) corresponding to the M3c domain (rat N11, FIG. 3A). Two additional rats had antibodies that bound to peptides 54/55 (amino acids 541-566; rat N52, FIG. 3D) which mapped to the preM1 domain. The preM1, M4n and M3c regions form part of the extracellular vestibule of the NMDA receptor channel where amino acid substitutions at key residues have a significant influence on channel permeability (Beck et al. (1999) *Neuron* 22: 559).

The AAVNMDAR1 vaccinated rats generated autoantibodies which were polyclonal. Epitope mapping of the antibodies showed a diverse range of epitopes in multiple regions of the extracellular domains. Individual animals had antibodies which bound to 16 mers that mapped to the extracellular vestibule of the channel including the preM1, M3c, M4n domains (Beck et al. (1999). *Neuron* 22: 559), as well as epitopes in the N terminal region and within the extracellular loop lying between M3 and M4 which directly mapped to glycine binding sites (Kuryatov et al. (1994) *Neuron* 12, 1291; Wafford et al. (1995) *Mol. Pharmacol.* 47, 374; Wood, et al. (1997) *J. Biol. Chem.* 272, 3532). Several animals did not appear to have an immunodominant epitope using the set of overlapping 16 mers, a result consistent with antibodies which are dependent on the conformational state of the protein.

In summary, rats were immunized against a specific brain protein, the NMDAR1 subunit of the NMDA receptor, and autoantibodies to the receptor were generated. These antibodies were able to bind to the NMDA receptor demonstrating specific targeting of a functional domain of the protein. The epitope-mapping analysis demonstrated that the autoantibodies bound to known functional regions of the protein including the extracellular vestibule of the channel as well as to peptides which contained glycine binding sites.

Example 3

Neuroprotection Against Epilepsy using the NMDAR1 Genetic Vaccine

To assess the anti-epileptic and neuroprotective efficacy of AAVNMDAR1 vaccination, the kainate model of temporal lobe epilepsy was used as described in Example 1L. The systemic administration of kainate is a well established model of temporal lobe epilepsy (See Sperk (1994) *Prog. Neurobiol.* 42: 1). Animals received AAVNMDAR1 (n=9) or AAVlac (n=8) and a group of naïve control rats received no vector (n=17). At one month following vaccination, animals were administered 10 mg/kg kainic acid intraperitoneally and a blinded observer determined over 2 hours whether there were any signs of the characteristic progression through various behavioural seizure stages, including immobility and staring, 'wet-dog-shakes', facial clonus, unilateral and bilateral forelimb clonus (Sperk (1994) *Prog. Neurobiol.* 42: 1)

FIG. 4 shows that kainate-induced seizure activity was evident shortly after drug administration as shown by EEG recordings. The first signs of electrographic seizure activity was observed within 10 minutes following drug administration in control animals, with 13 out of 17 naïve and 6 of the 8 AAVlac animals developing facial and forearm clonus and proceeding to status epilepticus (SE). In contrast, only 2 out of the 9 AAVNMDAR1-vaccinated animals developed seizures and SE (Table 1). The remaining 7 AAVNMDAR1 rats showed neither EEG changes nor any behavioural changes following kainate (p=0.007, Chi Square analysis with expected SE frequency of 68% reduced to 22% in the NMDAR1-immunized group). In those rats which exhibited SE, seizures were terminated with an anticonvulsant dose of sodium pentobarbital (30 mg/kg i.p.) after 45 minutes. Animals that did not develop seizures also received pentobarbital (30 mg/kg i.p.).

To confirm that the AAVNMDAR1 vaccination was able to suppress kainate-induced seizures, the hippocampi of all animals was examined for any signs of seizure-induced neuropathology. Three days after kainate treatment, animals were euthanised and then brains were removed and frozen and coronal hippocampal sections were prepared for immunohistochemistry and analysed using TUNEL and clusterin analysis, as described in Example 1 G and H.

Analysis of hippocampal damage using fluorescent TUNEL labelling, and using clusterin immunohistochemistry combined with immunohistochemistry with NeuN, a mature neuronal marker. As shown in the hilar region, all AAVlac animals that developed SE showed numerous TUNEL-positive (arrows) and clusterin-immunofluorescent neurons, indicative of extensive neuronal death in the hippocampus. No TUNEL or clusterin immunofluorescence was found in any AAVNMDAR1-vaccinated rat that did not have seizures.

One AAVNMDAR1-vaccinated rat that developed SE also showed extensive clusterin and TUNEL staining. Of interest, the second animal that developed SE showed no TUNEL signal or clusterin immunofluorescence. The EEG recordings shown in (FIG. 4) correspond to the brains analyzed. Kainate-induced seizures were also elicited in AAVGAD65-vaccinated animals and TUNEL and clusterin labelling confirmed extensive neuronal damage in the hippocampus. Scale 200 μm.

The results demonstrated that no discernible TUNEL signal or clusterin immunofluorescence (a cell death marker, see Dragunow et al. (1995) *Mol. Brain Res.* 32: 279) was observed in the hippocampus of any animal (AAVlac, naïve or AAVNMDAR1) that did not develop SE. In comparison, all AAVlac and naïve animals that experienced SE had numerous TUNEL-positive and clusterin-immunofluorescent neurons in hippocampal CA1, CA3 and hilar regions. Of the two AAVNMDAR1 animals that had SE, only one of these animals (rat N12) had some injury, whereas the second animal (N7) had no injury whatsoever, despite over 45 minutes of severe SE (Table 1).

As seizure duration is a critical determinant of the extent of neuronal injury, with as little as 30 minutes duration being sufficient to cause cell death (Lothman et al. (1993) *Epilepsia* 34: S59), these results suggest that the AAVNMDAR1 vaccination can not only produce resistance to seizures but also protect against excitotoxic injury. Of interest, N12, the only rat to have SE as well as brain injury following AAVNMDAR1 oral dosing, was also the only animal of the 9 in this experiment that did not have detectable circulating antibodies to the NMDAR1 receptor subunit.

(i) NMDA Receptor Specificity

To determine whether the anti-epileptic and neuroprotective effect of the NMDAR1 vaccination was non-specific and could be reproduced with immunization against any brain protein, an AAV vector expressing glutamic acid decarboxylase-65 (GAD-65) was generated. The vector expressing GAD-65 was perorally administered to an additional group of rats. These rats all developed significant antibody titres to the native protein. At one month following vaccination, these rats were challenged with kainate as described above. All of these rats (n=6) rapidly progressed to motor seizures and SE (Table 1). Analysis of their brains showed extensive damage (FIGS. 4J, K confirming severe seizure activity. These results demonstrate the specific involvement of NMDA receptors in epilepsy.

TABLE 1

Summary data showing the neuroprotective effect on epilepsy in rats vaccinated with the AAVNMDAR1 vaccine

|  | Number developing SE | Hippocampal injury in SE rats | | |
|---|---|---|---|---|
|  |  | − | ++ | +++ |
| Naïve | 13 (17) | — | — | 13 |
| AAVlac | 6 (8) | — | — | 5 |
| AAVNMDAR1 | 2 (9) | 1 | 1 | — |
| AAVGAD-65 | 6 (6) | — | — | 6 |

Hippocampal injury in rats that had developed SE was graded according to the extent of injury, − no injury, ++ moderate (<20 TUNEL or clusterin-immunofluorescent cells), +++ extensive (>20 TUNEL or clusterin-immunofluorescent cells). Numbers in parentheses represent total number of rats in that group. No injury was found in rats that did not develop SE.

(ii) Antibody Passage Across an Intact Blood-Brain Barrier

To confirm passage of NMDAR1 antibodies into the brain, at 4 weeks a group of vaccinated rats (n=4) underwent non-traumatic sampling of cerebrospinal fluid (CSF) from the cisterna magna. FIG. 5A shows the results of an immunoblot analysis of AAVlac, AAVNMDAR1 serum and CSF and AAVGAD serum. 30 micrograms of hippocampal membrane extract was separated on a reducing gel under non-denaturing conditions. Sera (1:5000) from AAVlac, AAVNMDAR1, AAVGAD and naïve rats were screened for the presence of NMDAR1 antibodies; (lane 1, polyclonal NMDAR1 antibody (Chemicon AB1516, 1:5000); lane 2, naïve sera; lane 3, AAVlac sera; lane 4, AAVNMDAR1 sera; lane 5, AAVGAD sera). CSF (1:5) from the same animals was also screened for NMDAR1 antibodies; (lane 6, naïve CSF; lane 7, AAVlac CSF; lane 8, AAVNMDAR1 CSF under basal conditions; lane 9, CSF from the same rat sampled 2 h after kainate administration). Serum from AAVGAD-65-vaccinated rats was screened for the presence of GAD65 antibodies against a hippocampal extract using immunoblot analysis. (Lane 1, commercial GAD65 antibody, Lane 2, 3 serum from two individual animals 1 month after vaccination).

Figure 5B:
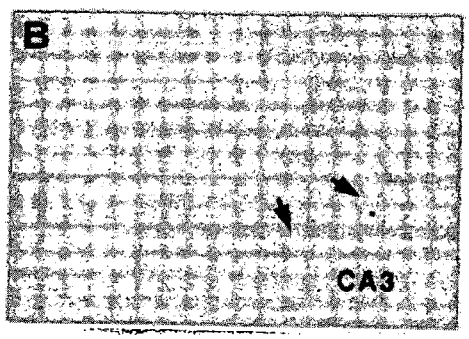
FIGS. 5B-D are photographs of the hippocampal region of the brain using anti-rat IgG immunohistochemistry and demonstrating that IgG penetration was significantly enhanced in the hippocampus following kainate treatment in the hilus and CA2-CA3 region (FIG. 5B, arrows).
Figure 5C:
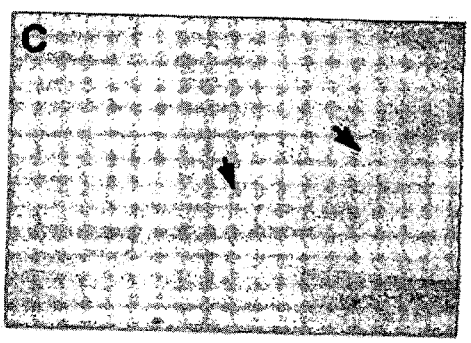
Figure 5D:
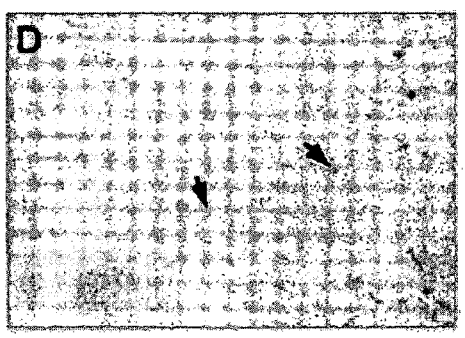
Figure 5E:
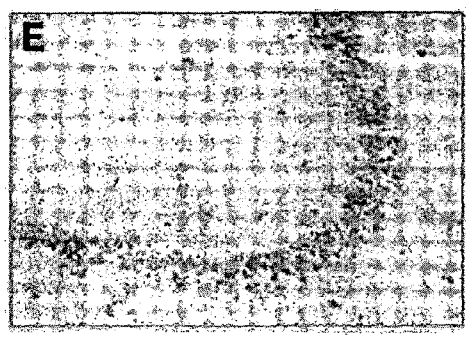
FIGS. 5E and 5I are images of immunohistochemistry analysis conducted on control hippocampal sections using IgG purified from AAVNMDAR1 rat serum.
Figure 5F:
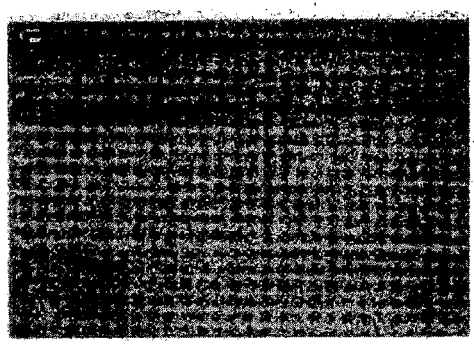
FIGS. 5F and 5H are images of immunohistochemistry analysis conducted on control hippocampal sections using IgG purified from AAVlac rat serum or naïve rat serum (not shown).
Figure 5G:
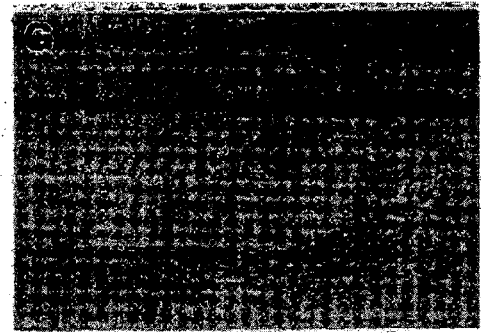
Figure 5H:
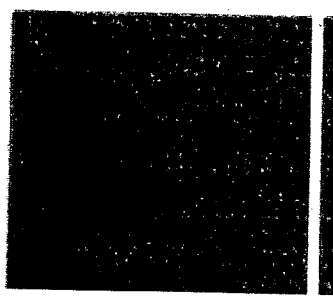
Figure 5I:
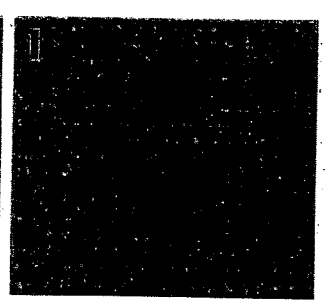
Figure 5J:

FIGS. 5B-D show the results of anti-rat IgG immunohistochemistry showing IgG penetration was significantly enhanced in the hippocampus following kainate treatment in the hilus and CA2-CA3 region (FIG. 5B, arrows). FIG. 5C is a high powered image of the CA3 region in (FIG. 5B) compared to the same region under basal conditions (arrows, FIG. 5D). Immunohistochemistry was conducted on control hippocampal sections using IgG purified from AAVNMDAR1 (FIGS. 5E, I), AAVlac (FIGS. 5F, H) or naïve rat serum (not shown). As shown in the CA3 (FIGS. 5E-G) and hilar region (FIGS. 5H-J), only AAVNMDAR1 purified IgG showed a selective immunoreactive staining pattern which was similar to that found with a commercial polyclonal NMDAR1 antibody (FIGS. 5G, J), while both naïve and AAVlac IgG (FIGS. 5F, H) produced only low level background staining Scale in FIG. 5B was 500 μm, in FIGS. 5C, D, E-F, was 20 μm, and in FIGS. 5H-J was 80 μm.

Using immunoblot analysis and a highly sensitive chemiluminescent detection method, NMDAR1 autoantibodies detected in the serum of AAVNMDAR1-vaccinated rats were also detected at low levels in the CSF by immunoblotting, demonstrating autoantibody passage into the brain (FIG. 5A). NMDAR1 autoantibodies were not detected in CSF from naïve (n=4) or AAVlac (n=4) immunised rats. Following kainate treatment, an approximate 10-fold increase in CSF levels of NMDAR1 autoantibodies was observed (FIG. 5A). In addition, IgG immunoreactivity was specifically increased in the hippocampus in the CA3 and dentate hilar neurons which are also susceptible to kainate-induced neuronal damage but which were protected in NMDAR1-immunized rats (FIGS. 5B-D). Furthermore, immunohistochemistry using IgG purified from AAVNMDAR1, AAVlac or naïve serum was conducted on hippocampal sections from naïve animals that had been perfused with PBS to remove endogenous IgG present in blood vessels. Only AAVNMDAR1-purified IgG showed selective immunoreactivity in hippocampal CA3, dentate hilar and CA1 neurons consistent with the pattern of expression of NMDAR1 using a commercial polyclonal antibody (FIGS. 5E-J).

A splenocyte proliferation assay was also used to investigate whether was is a cellular-mediated immune component associated with the vaccine. No difference in proliferative response was found between splenocytes isolated from AAVlac and AAVNMDAR1 animals challenged with the appropriate antigen (results not shown). In addition, immunohistochemistry with CD8+ and MHC Class I antibody markers on hippocampal sections from naïve, AAVlac and AAVNMDAR1 rats showed no difference in CD8+ or MHC Class I immunoreactivity suggesting that the likely mechanism of action of the vaccination is mediated through a humoral response and is consistent with the association between antibody titre and the neuroprotective phenotype observed.

In summary, the results demonstrate that in serum antibody titres obtained from vaccinated animals, low levels of NMDAR1 antibodies were detected in the CSF under basal conditions using a highly sensitive chemiluminescence detection system. However, a substantial increase in the antibodies was observed in the CSF following insult/injury to the blood-brain barrier by kainate administration.

A major limitation of the successful translation of promising NMDA receptor antagonists to the clinic has been the significant profile of CNS adverse effects associated with these drugs (Schehr (1996) *Nat. Biotechnol.* 14, 1549). The invention provides a vaccine or antibody approach to NMDA receptor antagonism with the advantage that the receptor blockade is minimal under resting physiological conditions where high serum titres of antibodies do not pass the blood-brain barrier efficiently. However, following a neuronal insult, the blood-brain barrier has increased permeability to serum antibodies, and transport and subsequent binding to the target protein can occur. This "on demand" or selective delivery of the neuroprotective agent (the autoantibody) limited both spatially to the site of injury and to the precise timing of injury is advantageous feature of the invention.

Of particular interest, glutamate itself alters blood-brain barrier permeability (Mayhan et al. (1996) *Stroke* 27, 965). Hence the vaccine strategy of the present invention may induce an autoprotective loop. Without being limited to a mechanism of action, a cerebral insult may increase brain extracellular glutamate, which increases blood-brain barrier permeability locally, resulting in facilitated passage of the autoantibody and antagonism of glutamate receptors.

Example 4

Neuroprotection Against Stroke Damage using the AAVNMDAR1 Vaccine

The endothelin-1 model of middle cerebral artery occlusion (MCAO) described by Sharkey et al. (1995) *J. Neurosci. Methods* 60: 125), was used to determine the anti-stroke and ischemic neuroprotection efficacy of AAVNMDAR1 vaccination. The model has been used previously to test novel anti-stroke drugs including the NMDA receptor antagonist, MK-801 (Sharkey et al. *Supra*, and Butcher et al. (1997) *J. Neurosci.* 17: 6939). This approach uses a fine needle to direct stereotactic delivery of endothelin-1 into the vicinity of the middle cerebral artery (MCA) and causes vasospasm leading to complete occlusion and generation of an extensive infarct in the MCA territory, including the stratium and cortex on the injected side.

Three groups of rats, untreated (n=10), AAVlac (n=8) and AAVNMDAR1 (n=10) underwent MCAO five months following vaccination. At 3 days following endothelin-1 administration, rats were euthanised, the brains removed and the infarct volume determined by a blinded investigator.

Figure 6H:
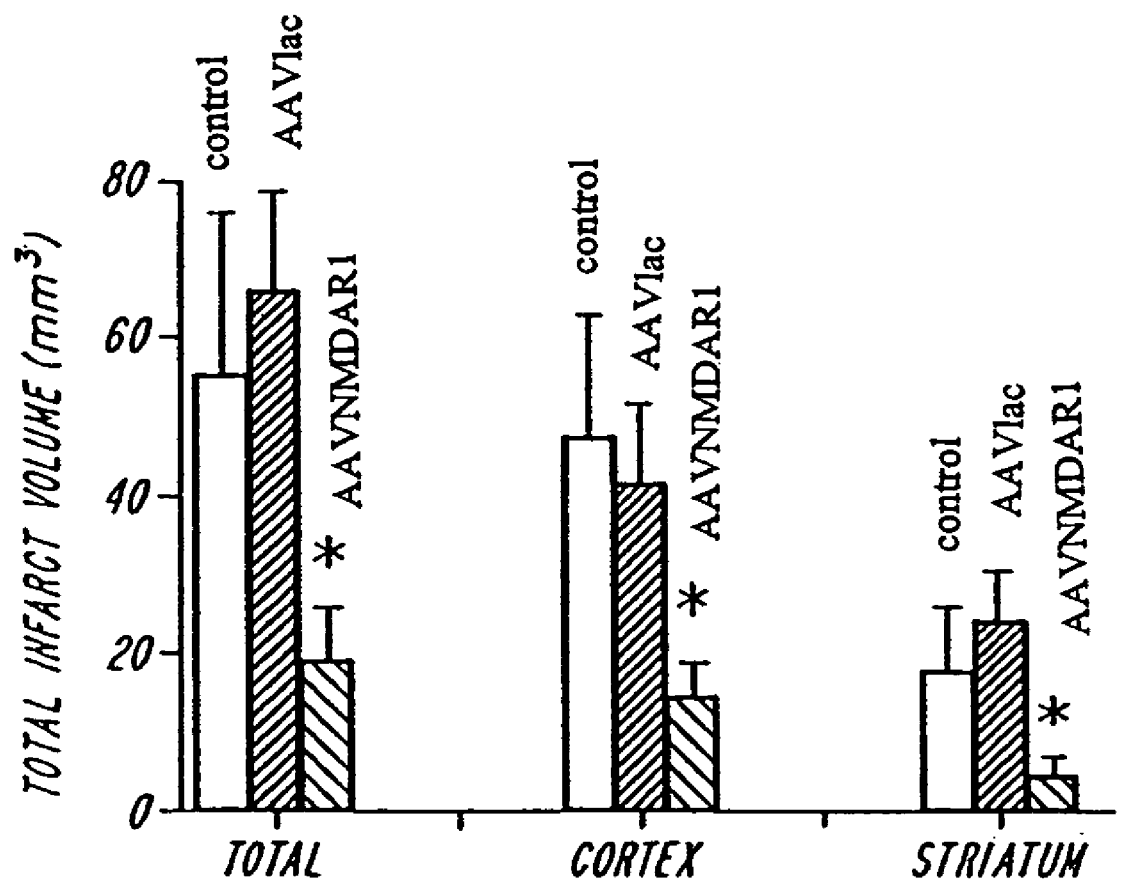
FIG. 6H is a bar chart showing the reduction in the total infarct volume of the cortex and striatum of AAVNMDAR1-vaccinated animals (n=10) (widely spaced downward sloping lines) compared to AAVlac-treated animals (n=8) (narrowly spaced upward sloping lines) or control naïve rats (n=10) (solid white). *P<0.01. Each bar represents the mean±SEM.

FIGS. 6A-6H show the results of the study. Three days following endothelin-induced MCAO, haematoxylin-eosin staining showed infarction of the ipsilateral stratium and/or cortical regions in AAVlac-treated animals (FIG. 6B) while there was no damage on the contralateral side (FIG. 6A). High power images of the undamaged contralateral (FIG. 6C) and infarcted ipsilateral (FIG. 6D) stratium. In contrast, damage was less severe and restricted to cortical regions in the AAVN-MDAR1-vaccinated animals (FIG. 6F) with no damage to the contralateral side (FIG. 6E and FIG. 6G). Increased isolectin B4 immunoreactivity in the infarcted regions suggests microglial proliferation into damaged areas (FIG. 6H). The total infarct volume was significantly less in the AAVNMDAR1-vaccinated group (n=10) compared to AAVlac-treated (n=8) or control naïve rats (n=10). *P<0.01. Each bar represents the mean+SEM. Scale for FIGS. 6A, B, E-G was 600 µm, and for FIGS. 6C-D was 100 µm.

The results demonstrate that the total infarct volume was 55.6+20.2 mm$^3$, in naïve rats and 66.4+12.4 mm$^3$ in the AAVlac animals, whereas in the AAVNMDAR1 rats the infarct was reduced by ~70% to 19.6+6.2 mm$^3$ (p=0.002, Student's t-test, FIG. 6H). When the cortex and stratium were analyzed independently, the protection in terms of infarct volume was 65% and 80% respectively compared to the AAVlac group and 69% and 74% compared to the naïve controls (FIG. 6H).

These results are of significant interest especially when considering that in partial stroke models, the most reproducible and potent data on neuroprotection has come from the use of NMDA receptor antagonists, particular the non-competitive compound, MK-801. However, even with this antagonist, at doses which depress motor activity, tissue rescue is limited to approximately 50% in the cortex with no infarct reduction in the stratium (Butcher et al. (1997) *J Neuorsci.* 17:6939-6946). Moreover, there is a narrow time window of only a few hours in which MK-801 and other promising new anti-stroke drugs need be given for rescue (Butcher et al. (1997) *J Neuorscl* 17:6939-6946) with effective protection requiring continued maintenance dosing (Steinberg et al. (1995) *Neuroscience* 64:99-107). Thus, the vaccination provides a neuroprotective effect against stroke damage.

Example 5

Vaccination Effects on Behaviour

To investigate whether the vaccination had any effect on the behaviour of the animals, the animals were tested using several established models of behaviour, (see Example 1R). Receptor antagonists administered systemically at anti-epileptic and neuroprotective doses typically result in some impairment in motor behaviour (Wozniak et al. (1990) *Pschopharmacol.* 101, 47). To determine whether vaccination was associated with any changes in motor behaviour, rats were tested on circular track and line crossing mobility paradigms For the line crossing mobility test, a 2 meter diameter circular table was divided into 9 segments of equal size. Each rat was placed in the center of the table, and allowed 5 minutes of free movement. During this time, a record was made of the number of times the rats two front feet crossed a line separating two segments. Testing was conducted for five days, with each animal receiving one trial per day. Between trials the table was cleaned with 70% ethanol.

Figure 7A:
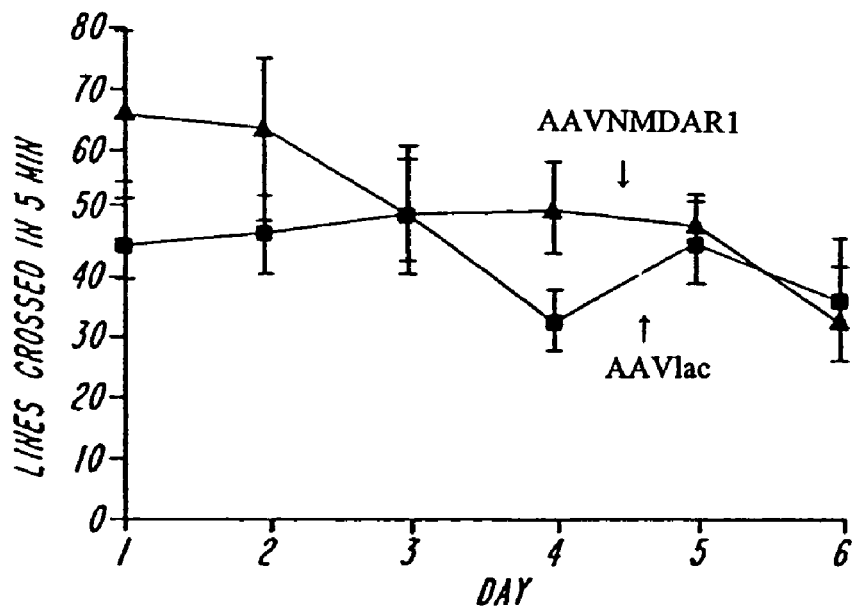
FIG. 7A is a graph showing the effect of vaccination of the behavior of rats in a line crossing test. Data represents the number of line crossings in 5 min intervals over 5 successive days in AAVlac-treated animals (squares-solid line) or AAVNMDAR1-vaccinated animals (triangle-solid line)
Figure 7B:
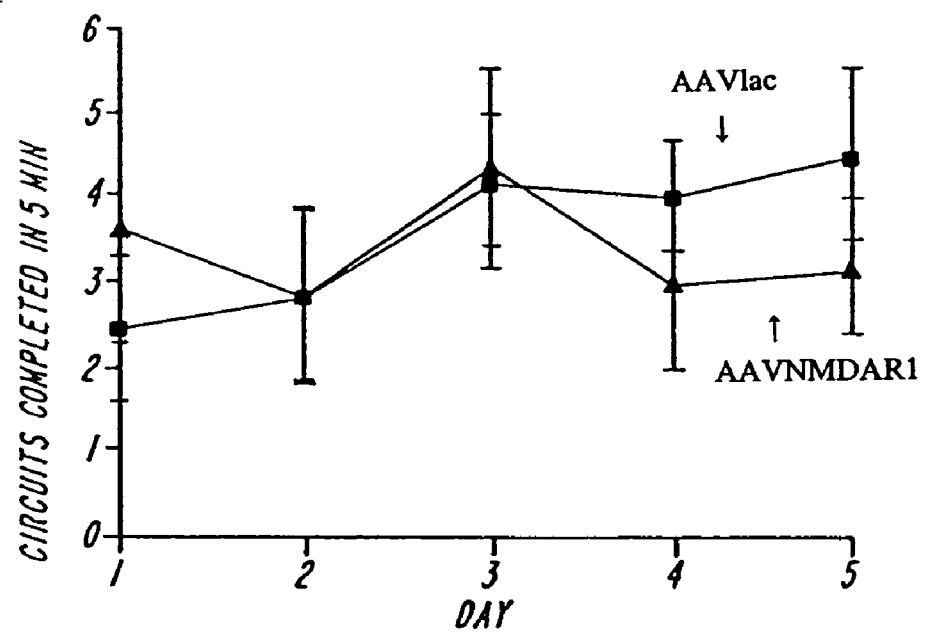
FIG. 7B is a graph showing the effect of vaccination of the behaviour of rats in a circular track mobility test. In the circular track test, the number of completed circuits in successive days for AAVlac-treated animals (n=6) and AAVNMDAR1-vaccinated animals (n=6)

For the circular track mobility test, the track used was a modified version of one used to test mobility in mice (Carlsson et al. (1990) *Life Sci.* 47: 1729). Each rat was placed inside the track at the start position, facing clockwise, and the number of circuits completed in 5 minutes was recorded. This procedure was conducted for 5 days. FIG. 7A depicts the results from the line crossing test and FIG. 7B depicts the results from the circular track mobility test. Data represents the number of line crossings in 5 min intervals over 5 successive days in AAVlac (squares-solid line) or AAVNMDAR1 rats (triangle-solid line). In the circular track test, the number of completed circuits in successive days for AAVlac (n=6) and AAVNMDAR1 (n=6) animals are represented.

The results from these behavioural studies did not demonstrate a difference between the groups of rats vaccinated compared with the control rats (repeated measures ANOVA, p=0.87 and p=0.32 respectively, FIGS. 7A-B). The results demonstrate that in contrast to the motor impairment associated with systemic administration of most pharmacological NMDA receptor blockers, the AAVNMDAR1 vaccinated rats had no impairment in locomotor function. Accordingly, the vaccine can be used for vaccination of individuals at risk of stroke and other cerebral insults without impairment of neurological function.

Example 6

Vaccination Effects on NMDA Receptor-Sensitive Gene Expression Using the AAVNMDRA1 Vaccine To demonstrate that vaccination with the AAVNMDAR1 vaccine modulates gene expression, adult rats were immunized by oral gavage with recombinant AAV vectors expressing either mouse NMDAR1 (AAVNMDAR1) or the *E. Coli* lacZ (AAVlac) cDNAs as previously described (During et al. 1998, supra) (also See Example 2). Serum was taken at one and four months for antibody titre and epitope mapping studies, as described in Example 1D.

(i) Modulation of NMDA Receptor Function

To demonstrate whether the purified IgG from the AAVNMDAR1 vaccinated rats would bind and influence the function of NMDA receptors expressed in primary neuronal cells grown in culture, primary mesencephalic rat neuronal cultures were incubated with IgG purified from AAVlac or AAVNMDAR1 rats. The cells were loaded with the calcium sensitive fluorescent dye, Oregon Green BAPTA-1, and the changes in fluorescent signal determined using confocal microscopy.

Figure 8:
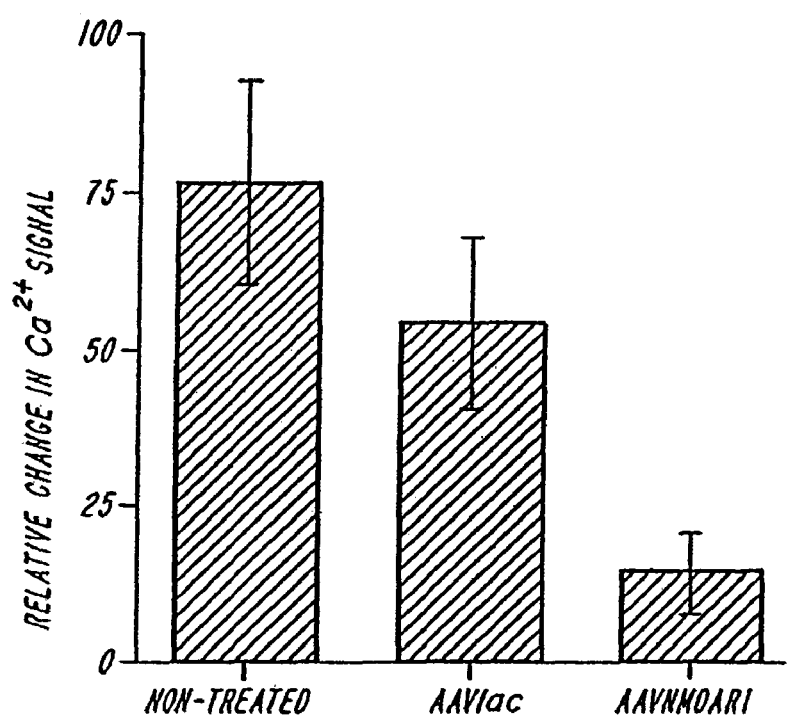
FIG. 8 is a bar chart showing the ratio of changes in fluorescent intensity relative to basal levels between AAVlac and AAVNMDAR1 IgG-treated cells.

The results from these studies are described below. Confocal images of non-treated control cells were taken. Confocal images were taken showing intracellular $Ca^{2+}$ imaging of cultured mesencephalic neurons and AAVNMDAR1 IgG inummoreactivity in mesencephalic and rat hippocampal neurons. NMDAR1 IgG-treated mesencephalic cells preloaded with the $Ca^{2+}$ indicator Oregon Green 488 BAPTA-1 (2 µM) showed low level fluorescence. Cells were preincubated with 50 µg/ml IgG for 16 h prior to indicator loading. In response to a 100 µM NMDA+3 µM glycine challenge, the increase in fluorescent signal found in non-treated control and AAVlac IgG-treated cells was significantly attenuated in AAVNMDAR1 IgG-treated cells. Images are pseudocoloured according to fluorescent intensity, with transition from red to yellow representing basal $Ca^{2+}$ levels to higher $Ca^{2+}$ concentrations (data not shown). FIG. 8 shows ratio of the changes in fluorescent intensity relative to basal levels showed a significant difference between AAVlac and AAVNMDAR1 IgG-treated cells. Each bar represents the mean±SEM, n=10 (*p=0.0012, Student's t-test). Anti-rat IgG immunocytochemistry showed only purified AAVNMDAR1 IgG bound to mesencephalic cells and not AAVlac IgG which exhibited basal immunoreactivity similar to non-treated cells. Using the IgG fractions to perform immunohistochemistry on brain sections, as shown in hippocampal hilar neurons, the AAVNMDAR1 IgG showed a pattern of immunoreactivity similar to that found with a commercial NMDAR1 polyclonal. antibody, while AAVlac IgG showed only low level background immunoreactivity.

The results show that in untreated cells, or cells incubated with IgG from AAVlac rats (n=10) at a concentration of 50 µg/ml, a marked increase in the fluorescent signal was obtained following NNMA application. Mesencephalic neurons incubated with the same concentration of IgG purified from AAVNMDAR 1-immunized rats (n=10) blocked the increase in intracellular calcium. Confirmation of specific binding was obtained by immunocytochemistry with a secondary anti-rat IgG which was applied to untreated primary mesencephalic cells or cells that had been incubated with AAVlac or AAVNMDAR1-purified IgG. The results showed that only IgG purified from AAVNMDAR1 rat serum bound to the primary neuronal cultures. These results demonstrate that the antibodies can directly modulate the function of the NMDA receptors.

(ii) Self-Antigen Recognition

To demonstrate the recognition of self-antigens by the serum of AAVNMDAR1-vaccinated rats, immunoglobulins were purified using protein G columns and used as the source of primary antibody for immunohistochemistry of rat brain sections (see Example 1D and 1G). Sections at the level of the hippocampus were selected, because NMDA receptors are highly expressed in this region. Purified IgG fractions from AAVlac rats showed low level background immunoreactivity in control hippocampal sections. In contrast, IgG purified from AAVNMDAR1 rats showed specific signals in CA1, CA3 and the hilus, consistent with previous reports on NMDAR1 immunoreactivity in the rat brain and similar to the pattern we observed with a commercial NMDAR1 polyclonal antibody.

(iii) Transport of Antibodies Across the Blood-Brain Barrier and NMDA Receptor Up Regulation.

Transport of the antibodies across the blood-brain barrier and subsequent binding to the native receptor on brain parenchyma tissue was investigated at basal physiological conditions. Groups of AAVlac (n=7) and AAVNMDAR I rats (n=7) were euthanised 4 weeks after peroral dosing of the vaccine and the brains were removed and frozen.

$^3$H-MK 801 autoradiography was used to label the open NMDA receptor channel in hippocampal sections using the technique described by Huettner et al. (Huettner et al. (1988) *Proc. Natl. Acad. Sci. U.S.A.* 85: 1307-1311) (see Example 10). Three markers of NMDA receptor binding were studied. These include $^3$H-MK-801 autoradiography, NMDAR1 immunohistochemistry with a commercial antibody and in situ hybridization with NMDAR1, NMDAR2a and NMDAR2b oligonucleotide probes showed increased binding, immunoreactivity and mRNA levels in AAVNMDAR1-vaccinated compared to AAVlac-treated hippocampus suggestive of NMDA receptor upregulation. In contrast, hippocampal mRNA levels of the trk B receptor in AAVlac and AAVNMDAR1 treated rats were not significantly different. The results showed an increase in $^3$H-MK-801 binding (arrows) in the hippocampus of AAVNMDAR-vaccinated rats. Relative density measurements from film autoradiograms showed there was a significant increase in soma and dendritic binding in the CA1 hippocampal region of AAVNMDAR1 compared to AAVlac animals (0.281±0.006 vs 0.2580±0.008; p=0.049, Student's t-test) while there was no significant difference in binding in the dentate granule cell or CA3 layer.

A commercial NMDA receptor-specific antibody was used to determine whether increased $^3$H-MK-801 binding was associated with an increase in NMDAR 1 protein expression. NMDAR1 rats had a significantly higher level of NMDAR1-immunoreactivity in the hippocampus (0.342±0.005 vs 0.314±0.002, p=0.0009, Student's t-test). Moreover, in situ hybridization using probes to NMDAR1, NMDAR2A and NMDAR2B subunits and density measurements of film autoradiograms also showed a highly significant increase in NMDAR1 (0.462±0.01 vs 0.356±0.016, p=0.0005) as well as the NNDAR2A (0.430±0.023 vs 0.378±0.009, p=0.038) and NNDAR2B (0.480±0.01 vs 0.430±0.015, p=0.019) mRNA.

The immunization effects were specific to these NMDAR mRNAs as no difference in mRNA levels of the trk B receptor were observed in either the dentate granule cell (AAVlac-0.310±0.009 vs AAVNMDAR1 0.314±0.005, p=0.706) or CA1 layer (0.308±0.009 vs 0.318±0.006, p=0.394). The changes in MK-801 binding, together with the increased NMDA receptor subunit transcripts and NMDA receptor immunoreactivity indicate passage of the antibody across the blood-brain barrier and partial antagonism of the receptor with a compensatory upregulation of NMDA receptors.

(iv) Modulation of Krox-24 Transcription Factor

To demonstrate that the antibodies are capable of indirectly modulating events involving the NMDA receptor, an indirect marker of NMDA receptor antagonism was examined. The expression of Krox-24 protein, a transcription factor whose cortical expression is maintained under tonic NMDA receptor activation, was investigated.

Immunohistochemical images of the cortex of animals were taken demonstrating antibody passage across an intact blood-brain barrier and the reduction of basal levels of Krox-24 protein within the cortex of AAVNMDAR1-vaccinated animals compared to AAVlac-treated, or naïve animals. High-powered images of Krox-24 immunoreactivity were also recorded. Anti-rat IgG immunohistochemistry used to investigate BBB penetration of IgG under basal conditions showed a weak but increased level of immunoreactivity in the cortex of AAVNMDAR1-treated when compared to AAVlac (FIG. 10E) or naïve animals. IgG penetration was significantly enhanced 90 min following kainate treatment, with specific increases in CA2-CA3 hippocampal regions compared to the same region under basal conditions. An immunoblot analysis of CSF sampled from an AAVlac (Lane 1) and AAVNMDAR1 animal (Lane 2) showed detection of a 117 ka protein species and breakdown products only from AAVNMDAR1 CSF under basal conditions. Increased levels of these proteins were found 90 min following kainate treatment (Lane 3).

The results demonstrate that antagonism of NMDA receptors using MK-801 leads to a significant decrease in Krox-24 expression. In AAVNMDAR1 (n=6) but not AAVlac (n=5) or naïve control rats (n=4), a 21±3.5% (p=0.038, NMDAR1 vs. lac, Student's t-test) a decrease in Krox-24 protein expression was observed in the cortex.

To further confirm passage of autoantibodies across the blood-brain barrier, the CSF was screened for the presence of NMDAR1 antibodies as described in Example 3(ii). Low levels of a 117 kD protein, consistent with the molecular weight of the native NMDAR 1 receptor subunit and breakdown products similarly recognized by commercial antibodies were detected in the CSF. Furthermore, levels of these protein species were increased following kainate treatment. In addition, brain sections of immunized rats were stained with an anti-rat IgG antibody to look at immunoglobulin transport into brain parenchyma. Under resting conditions, an increase in brain anti-IgG binding was observed in AAVNMDAR1 rats compared to naïve or AAVlac rats. Following kainate administration, a further increase in the anti-IgG immunoreactivity was apparent in hippocampal sections from AAVNMDAR1 rats consistent with the CSF immunoblot result.

(v) Effect of the Vaccine on Inflammation in the Brain

To determine whether there was any inflammatory response, cellular infiltrate or microglial reaction due to vaccination with AAVNMDAR1 vaccination, sections of the brain were analysed. No inflammatory responses were observed in the brain. Similar levels of basal isolectin-B4, OX-18 and CD8 immunoreactivity in the cortex of naïve, AAVlac, AAVNMDAR1 suggested no inflammatory responses associated with vaccination. Scale A-1, 500 µm. The results showed that brain morphology appeared normal under light microscopy in vaccinated rats, and immunohistochemistry using antibodies to isolectin B4, a microglial marker (Streit, et al. (1987) J. Neurocytol. 16: 249-60), OX-18, an MHC Class I marker, and CD8, a cytotoxic T-cell marker, showed no differences between AAVNMDAR1, AAVlac and naïve control animals. The data therefore demonstrates the successful and stable NMDAR1 transgene expression over a period of five months without an inflammatory response.

In summary, the results demonstrate that purified antibodies from AAVNMDAR1 rats specifically bound to hippocampal neurons and the pattern of immunoreactivity mirrored that obtained using commercial NMDA receptor antibodies. Furthermore, antibodies from AAVNMDAR1 rats specifically bound to, and antagonized the NMDA-induced increase in the calcium signal in primary neurons, whereas serum from naïve rats or from rats immunized with the control AAVlac vector did not. Attenuation of the calcium signal suggests that the autoantibodies bind to and inhibit NMDA receptors.

Indirect support for in vivo antagonism of NMDA receptors was demonstrated by examining the change in expression of the transcription factor, Krox-24. Notably, the basal expression of Krox-24 has previously been shown to be under glutamatergic tonic activation and pharmacological antagonism of NMDA receptors inhibit cortical levels of the protein (Gass et al. (1993) Neuroscience 53: 749-758). AAVNMDAR1-immunized animals had a −20% decrease in basal Krox-24 expression consistent some passage of the antibody and inhibition of NMDA receptor mediated glutamatergic neurotransmission.

Additional evidence of blood-brain barrier passage and receptor antagonism was shown by the upregulation of NMDAR1 as well as NMDAR2A and NMDAR2B mRNA in hippocampal sections from AAVNMDAR1-immunized animals. This increase in the NMDA receptor subunit mRNA transcripts was associated with an increase in NMDA receptor protein, a result consistent with previous reports of increased NMDA receptor subunit mRNA levels following pharmacological antagonism of the receptor (Wilson et al. (1998) Dev. Brain Res. 109: 211-220). Even though the vaccine targeted just the NMDAR1 subunit, the NMDA receptor in vivo is not a homomeric complex composed of NNMAR1 subunits, but is invariably a heteromer made up with NMDAR2 subunits (Sheng et al. (1994) Nature 368: 144-147 and McBain et al. (1994) Physiol. Rev. 74: 723-760). Moreover, the expression of NMDAR1 and NMDAR2 subunits to be appear linked, and functional antagonism of the receptor leads to an upregulation of both NMDAR1 and NMDAR2 subunits (Wilson et al. (1998) supra; Fossom et al. (1995) Mol. Pharmacol. 48: 981-987). The results also showed no difference in hippocampal mRNA levels of NR2C, NR2D or the trk B receptor between AAVlac and AAVNMDAR1-immunized rats suggesting that the vaccination effects were specific to NMDA receptors.

Collectively, these results demonstrate that the genetic vaccine of the invention can be used for functional genomic studies to investigate the function of proteins expressed in the brain. The results describe a simple genetic vaccine to induce autoantibodies which target the gene of interest and thereby modify its function.

Example 7

Vaccination Effects on Rat Learning and Memory (Cognition)

To investigate the effect of the AAVNMDAR1 vaccine on learning and memory, the ingestive behaviour and body weights of rats vaccinated with the genetic vaccine were monitored. At weekly intervals following vaccination with no alteration in feeding or weight gain in either group.

At four months post-vaccination, rats underwent behavioural testing as described in Example 1R. One of the most sensitive behavioural tests for NMDA antagonists is impairment of performance in tasks that involve hippocampal-dependent learning and memory. NMDA receptor antagonists at effective neuroprotective doses typically interfere with learning in spatial navigation tasks (Bannerman, et al. (1995) Nature 378: 182-186), although newer generation compounds, particularly NMDA receptor antagonists that are partial agonists at the glycine binding site may facilitate learning in hippocampal tasks.

AAVNMDAR1-vaccinated rats were compared with AAVlac rats to determine whether the immunization was associated with impairment in a spatial maze task (Barnes (1979) J. Comp. Physiol. Psychol. 93: 74-104). FIG. 9 shows the results of AAVNMDAR1 vaccination effects on learning and memory.

Figure 9A:
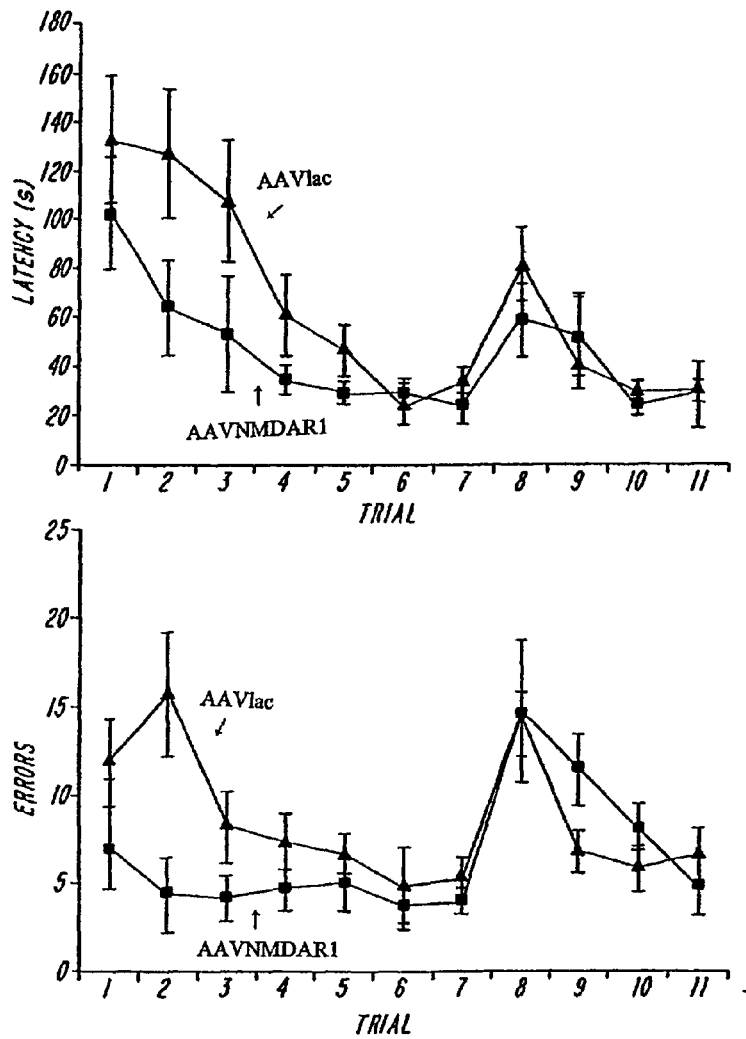
FIG. 9A demonstrates errors and latencies recorded on the Barnes Circular Maze test. Data represents the number of line crossings in 5 min intervals over 5 successive days in AAVlac (triangle-solid line) or AAVNMDAR1 rats (squares-solid line)
Figure 9B:
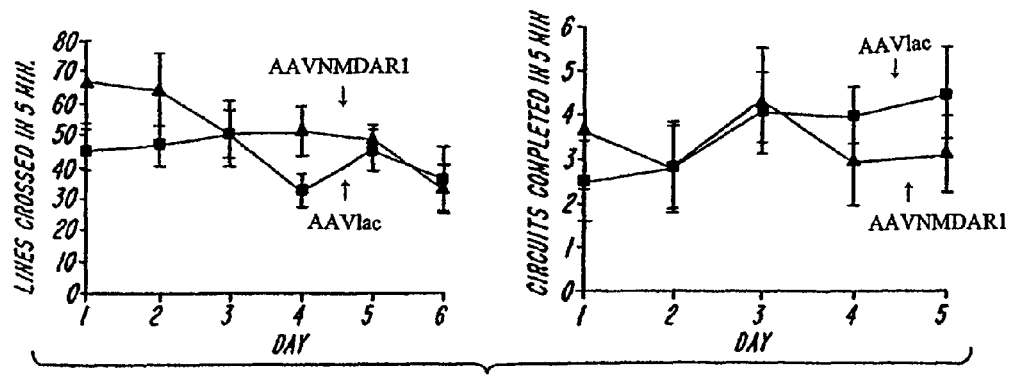
FIG. 9B demonstrates the line crossing and circular track mobility test in AAVlac (squares-solid line) or AAVNMDAR1 rats (triangle-solid line)

FIG. 9A is a graph showing errors and latencies recorded on the Barnes Circular Maze from AAVlac-treated rats, and AAVNMDAR1-vaccinated rats. FIG. 9B is a graph showing the results from the line crossing and circular track mobility tests. Data represents the number of line crossings in 5 min intervals over 5 successive days in AAVlac-treated, or AAVNMDAR1-vaccinated rats. In the circular track test, the number of completed circuits in successive days for AAVlac-treated and AAVNMDAR1-vaccinated animals are represented. FIG. 9C depicts the results from the contextual fear conditioning for AAVlac-treated and AAVNMDAR1-vaccinated animals ($*p=0.025$). FIG. 9D depicts the results from the Spontaneous Object Recognition test. The left graph is a comparison within groups of time spent exploring during the sample phase (A1 vs A2) and the choice phase (A3 vs B). The right graph is a comparison between groups of total time spent exploring in sample phase (A1+A2), choice phase (A3+B), and the discrimination index (B-A3). ($*p=0.041$).

Results showed that in the Barnes maze the AAVNMDAR1 rats (n=15) had significantly improved performance compared to AAVlac rats (n=16) as defined by reduced latencies to enter the escape box (repeated measures ANOVA, $p=0.043$, FIG. 9A). Improved performance in the Barnes maze may be due to other factors such as increased mobility. To examine increased mobility, the rats were tested on circular track and line crossing mobility paradigms, both of which failed to demonstrate a difference between the groups (repeated measures ANOVA, $p=0.87$ and $p=0.32$ respectively, FIG. 9B).

NMDA receptor activation has also been demonstrated to be involved in the storage of other forms of memory, such as contextual memory (Kiyama et al, (1998) J. Neurosci. 18; 6704-6712 and object recognition memory (Puma et al. (1998) Neurosci. Lett. 244: 97-100). To assess whether the vaccinated rats had an improved contextual memory, the rats were tested for their freezing responses. The results demonstrated that AAVNMDAR1-vaccinated rats (n=12) exhibited a stronger freezing response than AAVlac rats (n=10) when placed in an environment in which a mild electric shock had been previously received ($p=0.025$, FIG. 9C). In addition, AAVNMDAR1 rats (n=19) discriminated and explored a novel object for significantly longer than an object previously encountered compared to AAVlac rats (n=16), ($p=0.041$, FIG. 9D).

These surprising results demonstrate the significant improvement in learning and memory in the AAVNMDAR1-vaccinated rats. The result obtained using the hippocampally-dependent Barnes circular platform task (Barnes, 1979, supra) was also generalizable to a novel object recognition task (Puma et al., 1998, supra), and a contextual association task ((Kiyama et al. (1998) supra). The improved learning and memory observed in the present invention may be due to the increase in the NMDA receptor number, perhaps compensating for antagonism of the receptor. Increases in NMDA receptor expression mediate experience-dependent synaptic plasticity in the visual cortex (Quinlan et al. (1999) Nat Neurosci. 2: 352-357). Furthermore, transgenic mice which overexpress NMDAR2B and NMDAR1 in the forebrain exhibit improved learning and memory associated with facilitation of synaptic potentiation (Tang et al. (1999) Nature 401: 63-69).

The gain of function demonstrated by the significant improvement in learning and memory, may be associated with an increase in transcription and translation of the targeted gene. Targeted autoimmunity using genetic vaccines may therefore provide not only the novel therapies to treat neurological disorders, but also a tool to analyze the function of genes.

Example 8

Vaccination Effect on Nociception

To investigate the effect of vaccination on pain tolerance associated with NMDA receptors, the tail-immersion and hot-plate pain assays were employed (Taulbee and Kasting (1988) J. Pharmacol. Methods 20: 197-206) (see Example 1S). These assays were used to determine whether AAVNNDAR1 immunized rats had altered responses to painful stimuli. The NMDA receptors have also been implicated in nociception (Nasstrom et al. (1992) Eur. J. Pharmacol. 212, 21-29). NMDA receptors mediate the release of substance P in the spinal cord (Liu et al. (1997) Nature 386: 721-724) and direct intrathecal administration of NMDA lowers pain thresholds (Davis et al. (1999) J. Pharmacol. Exp. Ther. 289: 1048-1053). Conversely, NMDA receptor antagonists show analgesic activity (Coderre (1993) Eur. J. Neurosci. 5: 390-393).

FIG. 10 depicts the results vaccination effects on Nociception. The latency for escape responses for the tail immersion test and latency for escape responses or hindpaw licking in the hot plate test for AAVlac (black bars) and AAVNMDAR1 (white bars) animals. Each bar represents the mean±SEM for all animals in that group ($*p=0.04$ for tail immersion and $p=0.02$ for hot plate tests, Student's t-test).

The results demonstrated that following tail immersion, AAVNMDAR1 rats (n=10) showed significantly longer latency to tail-flick than the AAVlac control rats (n=8), ($p=0.04$, FIGS. 10). Similarly, in the hot plate assay, the latency of the AAVNMDAR1 rats (n=8) was greater than the AAVlac animals (n=8), ($p=0.02$, FIGS. 10).

EQUIVALENTS

Those skilled in the art will recognize, or be able to ascertain using no more than routine experimentation, many equivalents of the specific embodiments of the invention described herein. Such equivalents are intended to be encompassed by the following claims.

The invention claimed is:

1. A composition to inhibit N-methyl-D-aspartate activity comprising:
   an adeno-associated virus vector comprising a nucleic acid sequence encoding for an N-methyl-D-aspartate (NMDA) receptor-1 antigen operably linked to a promoter and capable of being expressed in a subject to elicit production of NMDA receptor-1 antibodies that inhibit NMDA activity, and
   a pharmaceutically-acceptable carrier.

2. The composition of claim 1, wherein the produced antibodies bind to an NMDA-1 receptor in the central nervous system.

3. The composition of claim 1, wherein the composition is a preparation for oral administration.

4. A method comprising the step of administering to a mammalian subject in need thereof, prior to a neuronal insult, a composition comprising a pharmaceutically-acceptable carrier and an adeno-associated viral (AAV) vector comprising a nucleic acid sequence encoding for an N-methyl-D-aspartate (NMDA) receptor-1 antigen operably linked to a promoter, wherein expression of the antigen in the mammalian subject elicits production of NMDA receptor-1 antibodies, and whereby the produced NMDA receptor-1 antibodies pass across the blood-brain barrier into the central nervous system following the neuronal insult to inhibit NMDA activity.

5. A method comprising: administering a composition to a mammalian subject in need thereof to inhibit N-methyl-D-aspartate activity, said composition comprising a vector comprising a nucleic acid sequence encoding for an N-methyl-D-aspartate (NMDA) receptor-1 antigen operably linked to a promoter, and a pharmaceutically-acceptable carrier, wherein said administering is prior to a neuronal insult, wherein the antigen is expressed and elicits the production of NMDA receptor-1 antibodies in the circulatory system of the mammalian subject which bind to an NMDA receptor-1 in the central nervous system to ameliorate epilepsy or stroke in the mammalian subject.

6. The method of claim 5, wherein the vector is a viral vector.

7. The method of claim 6, wherein the viral vector is selected from the group consisting of an adeno-associated virus vector, an adenovirus vector, a herpes virus vector, a parvovirus vector, and a lentivirus vector.

8. The method of claim 7, wherein the viral vector is an adeno-associated virus vector.

9. The method of claim 5, wherein the composition further comprises a colloidal dispersion system.

10. The method of claim 5, wherein the composition further comprises an injectable particle coated with the nucleic acid sequence.

11. The method of claim 5, wherein the composition is a preparation for oral administration.

12. The method of claim 5, wherein the composition is a preparation for intravenous injection.

13. The method of claim 5, wherein the composition is a preparation for intramuscular injection.

* * * * *

SEQUENCE LISTING

<160> NUMBER OF SEQ ID NOS: 7

<210> SEQ ID NO 1
<211> LENGTH: 21
<212> TYPE: DNA
<213> ORGANISM: cytomegalovirus

<400> SEQUENCE: 1
cccagtacat gaccttatgg g                                         21

<210> SEQ ID NO 2
<211> LENGTH: 20
<212> TYPE: DNA
<213> ORGANISM: cytomegalovirus

<400> SEQUENCE: 2
ggagacttgg aaatccccgt                                           20

<210> SEQ ID NO 3
<211> LENGTH: 19
<212> TYPE: DNA
<213> ORGANISM: cytomegalovirus

<400> SEQUENCE: 3
ctcttccagc cttccttcc                                            19

<210> SEQ ID NO 4
<211> LENGTH: 19
<212> TYPE: DNA
<213> ORGANISM: cytomegalovirus

<400> SEQUENCE: 4
gtcaccttca ccgttccag                                            19

<210> SEQ ID NO 5
<211> LENGTH: 43
<212> TYPE: DNA
<213> ORGANISM: murine

<400> SEQUENCE: 5
cacagcctgg atggcctcag ctgcgctctc gtaattgtgt ttt                 43

<210> SEQ ID NO 6
<211> LENGTH: 37
<212> TYPE: DNA
<213> ORGANISM: murine

<400> SEQUENCE: 6
agaaggcccg tgggagcttt ccctttggct aagtttc                        37

<210> SEQ ID NO 7
<211> LENGTH: 45
<212> TYPE: DNA
<213> ORGANISM: murine

<400> SEQUENCE: 7
catgttcttg gccgtgcgga gcaagcgtag gatgttggag tgggt               45